(12) United States Patent
Ihara et al.

(10) Patent No.: US 7,273,879 B2
(45) Date of Patent: Sep. 25, 2007

(54) THIADIAZOLE COMPOUNDS AND USE THEREOF

(75) Inventors: Hideki Ihara, Osaka (JP); Noriyasu Sakamoto, Toyonaka (JP); Hiroki Tomioka, Ikeda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 533 days.

(21) Appl. No.: 10/498,651

(22) PCT Filed: Jan. 15, 2003

(86) PCT No.: PCT/JP03/00237

§ 371 (c)(1),
(2), (4) Date: Jun. 10, 2004

(87) PCT Pub. No.: WO03/059897

PCT Pub. Date: Jul. 24, 2003

(65) Prior Publication Data

US 2005/0215578 A1 Sep. 29, 2005

(30) Foreign Application Priority Data

Jan. 17, 2002 (JP) ............................. 2002-008356

(51) Int. Cl.
C07D 285/08 (2006.01)
A01N 43/836 (2006.01)

(52) U.S. Cl. ..................................... 514/361; 548/130

(58) Field of Classification Search ................ 514/361; 548/130
See application file for complete search history.

(56) References Cited

U.S. PATENT DOCUMENTS

| | | | |
|---|---|---|---|
| 4,067,720 A | 1/1978 | Perronnet et al. | |
| 4,069,319 A | 1/1978 | Perronnet et al. | |
| 4,692,457 A | 9/1987 | West et al. | |
| 5,827,800 A | 10/1998 | Forster et al. | |
| 6,605,631 B1 | 8/2003 | Kirstgen et al. | |
| 2006/0014962 A1* | 1/2006 | Ihara | 548/129 |

FOREIGN PATENT DOCUMENTS

| | | | |
|---|---|---|---|
| DE | 2914003 | * | 10/1980 |
| DE | 30 30 661 A1 | | 4/1982 |
| EP | 0 623 604 A2 | | 11/1994 |
| EP | 0 757 042 A1 | | 2/1997 |
| EP | 0 623 604 B1 | | 8/2001 |
| JP | 2002-338557 A | | 11/2002 |
| WO | WO94/19331 A1 | | 9/1994 |
| WO | WO98/05652 A2 | | 2/1998 |

OTHER PUBLICATIONS

Teruhisa Noguchi, "Studies on the Selective Toxicity. VIII. ⁿBiological Activities of 1,2,4-Thiadiazole Derivatives", *Yakugaku Zasshi*, pp. 1437-1449, (1968).

* cited by examiner

*Primary Examiner*—Rebecca Anderson
*Assistant Examiner*—Andrew B. Freistein
(74) *Attorney, Agent, or Firm*—Akin Gump Strauss Hauer & Feld LLP

(57) ABSTRACT

A thiadiazole compound of the formula (A):

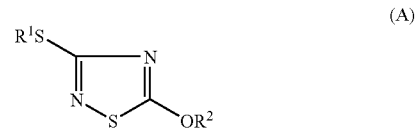

(A)

wherein $R^1$ represents methyl, C3-C7 alkenyl, C2-C7 alkoxyalkyl, C2-C7 alkylthioalkyl, C4-C7 alkoxyalkoxyalkyl, C4-C7 alkylthioalkoxyalkyl, phenyl C1-C2 alkyl in which phenyl may be substituted, phenyloxy C1-C2 alkyl in which phenyloxy may be substituted, phenyl C2-C3 alkoxyalkyl in which phenyl may be substituted, or the substituent of the formula (B):

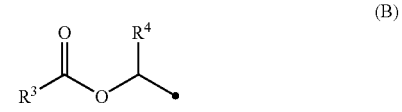

(B)

wherein $R^3$ represents C1-C3 alkyl, and $R^4$ represents a hydrogen atom, methyl, ethyl or phenyl which may be substituted; and
$R^2$ represents phenyl C1-C4 alkyl in which phenyl may be substituted, pyridyl C1-C4 alkyl in which pyridyl may be substituted, or pyrimidyl C1-C4 alkyl in which pyrimidyl may be substituted;
has an excellent arthropod pests controlling activity.

11 Claims, No Drawings

THIADIAZOLE COMPOUNDS AND USE THEREOF

CROSS-REFERENCE TO RELATED APPLICATIONS

This application is a section 371 national phase filing of International Application No. PCT/JP03/00237, filed Jan. 15, 2003, the disclosure of which is incorporated herein by reference.

TECHNICAL FIELD OF THE INVENTION

The present invention relates to a thiadiazole and uses thereof.

BACKGROUND ART

It is known wherein a kind of thiadiazole compound can be used as an active ingredient in an arthropod pests controlling composition (cf. DE 3030661 publication).

However the arthropod pests controlling activity of the thiadiazole compound is not efficient, then it is desired the compounds having more efficient arthropod pests controlling activity.

DISCLOSURE OF THE INVENTION

The present inventor has earnestly studied, and found wherein a thiadiazole compound of the formula (A) has excellent arthropod pests controlling activity to complete the present invention.

Namely, the present invention provides the thiadiazole compound (hereinafter, referred to as the present compound) of the formula (A):

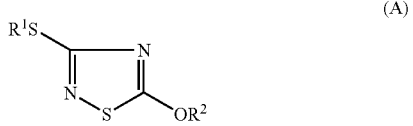

wherein $R^1$ represents methyl, C3-C7 alkenyl, C2-C7 alkoxyalkyl, C2-C7 alkylthioalkyl, C4-C7 alkoxyalkoxyalkyl, C4-C7 alkylthioalkoxyalkyl, phenyl C1-C2 alkyl in which phenyl may be substituted, phenyloxy C1-C2 alkyl in which phenyloxy may be substituted, phenyl C2-C3 alkoxyalkyl in which phenyl may be substituted, or the substituent of the formula (B):

wherein $R^3$ represents C1-C3 alkyl, and $R^4$ represents a hydrogen atom, methyl, ethyl or phenyl which may be substituted; and $R^2$ represents phenyl C1-C4 alkyl in which phenyl may be substituted, pyridyl C1-C4 alkyl in which pyridyl may be substituted, or pyrimidyl C1-C4 alkyl in which pyrimidyl may be substituted;

the arthropod controlling composition comprising the present compound as an active ingredients;

and the method for controlling an arthropod pest comprising applying an effective amount of the present compound to an arthropod pest or habitats of an arthropod pest.

In the present invention, each substituent represented by $R^1$ or $R^2$ is specifically exemplified below.

The C3-C7 alkenyl, represented by R1, includes 2-butenyl, 3-methyl-2-butenyl, 2-pentenyl and the like.

The C2-C6 alkoxyalkyl, represented by R1, includes (C1-C6 alkoxy)methyl and the like; more specifically, methoxymethyl, ethoxymethyl, propoxymethyl, isopropoxymethyl and the like.

The C2-C7 alkylthioalkyl, represented by R1, includes (C1-C6 alkylthio)methyl and the like; more specifically, methylthiomethyl, ethylthiomethyl, propylthiomethyl, isopropylthiomethyl and the like.

The C4-C7 alkoxyalkoxyalkyl, represented by R1, includes (2-methoxyethoxy)methyl and the like.

The C4-C7 alkylthioalkoxyalkyl, represented by R1, includes (2-ethylthioethoxy)methyl and the like.

The phenyl C1-C2 alkyl in which phenyl may be substituted, represented by R1, includes C1-C2 alkyl substituted with phenyl which may be substituted with one or more selected from the group (hereinafter, referred to as the substitution group A) consisting of C1-C4 alkyl such as methyl, ethyl, propyl, isopropyl, tert-butyl and the like; C1-C4 haloalkyl such as trifluoromethyl, difluoromethyl, pentafluoroethyl and the like; C1-C4 alkoxy such as methoxy, ethoxy, propoxy, isopropoxy and the like; C1-C4 alkylthio such as methylthio, ethylthio and the like; C1-C4 haloalkoxy such as trifluoromethoxy, difluoromethoxy and the like; nitro; cyano; and halogen atoms such as a fluorine atom, chlorine atom, bromine atom and the like. More specifically it includes benzyl, 2-methylbenzyl, 3-methylbenzyl, 4-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 2-methylthiobenzyl, 3-methylthiobenzyl, 4-methylthiobenzyl, 2-trifluoromethoxybenzyl, 3-trifluoromethoxybenzyl, 4-trifluoromethoxybenzyl, 2-nitrobenzyl, 3-nitrobenzyl, 4-nitrobenzyl, 2-cyanobenzyl, 3-cyanobenzyl, 4-cyanobenzyl, 2-fluorobenzyl, 3-fluorobenzyl, 4-fluorobenzyl, 3,4-difluorobenzyl, 3,5-difluorobenzyl, 2,6-difluorobenzyl, 2,4-difluorobenzyl, 2-chlorobenzyl, 3-chlorobenzyl, 4-chlorobenzyl, 3,4-dichlorobenzyl, 3,5-dichlorobenzyl, 2,6-dichlorobenzyl, 2,4-dichlorobenzyl, 2-bromobenzyl, 3-bromobenzyl, 4-bromobenzyl, 3,4-dibromobenzyl, 3,5-dibromobenzyl, 2,6-dibromobenzyl, 2,4-dibromobenzyl, 1-phenylethyl, 1-(2-methylphenyl)ethyl, 1-(3-methylphenyl)ethyl, 1-(4-methylphenyl)ethyl, 1-(2-trifluoromethylphenyl)ethyl, 1-(3-trifluoromethylphenyl)ethyl, 1-(4-trifluoromethylphenyl)ethyl, 1-(2-methoxyphenyl)ethyl, 1-(3-methoxyphenyl)ethyl, 1-(4-methoxyphenyl)ethyl, 1-(2-methylthiophenyl)ethyl, 1-(3-methylthiophenyl)ethyl, 1-(4-methylthiophenyl)ethyl, 1-(2-trifluoromethoxyphenyl)ethyl, 1-(3-trifluoromethoxyphenyl)ethyl, 1-(4-trifluoromethoxyphenyl)ethyl, 1-(2-nitrophenyl)ethyl, 1-(3-nitrophenyl)ethyl, 1-(4-nitrophenyl)ethyl, 1-(2-cyanophenyl)ethyl, 1-(3-cyanophenyl)ethyl, 1-(4-cyanophenyl)ethyl, 1-(2-fluorophenyl)ethyl, 1-(3-fluorophenyl)ethyl, 1-(4-fluorophenyl)ethyl, 1-(3,4-difluorophenyl)ethyl, 1-(3,5-difluorophenyl)ethyl, 1-(2,6-difluorophenyl)ethyl, 1-(2,4-difluorophenyl)ethyl, 1-(2-chlorophenyl)ethyl, 1-(3-chlorophenyl)ethyl, 1-(4-chlorophenyl)ethyl, 1-(3,4-dichlorophenyl)ethyl, 1-(3,5-dichlorophenyl)ethyl, 1-(2,6-dichlorophenyl)ethyl, 1-(2,4-dichlorophenyl)ethyl, 1-(2-bromophenyl)ethyl, 1-(3-bromophenyl)ethyl, 1-(4-bromophenyl)ethyl, 1-(3,4- dibromophenyl)ethyl, 1-(3,5-dibromophenyl)ethyl, 1-(2,6-dibromophenyl)ethyl, 1-(2,4-dibromophenyl)ethyl, 2-phenylethyl, 2-(2-methylphenyl)ethyl, 2-(3-methylphenyl)ethyl, 2-(4-methylphenyl)ethyl, 2-(2-trifluoromethylphenyl)ethyl, 2-(3-trifluoromethylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2-methylthiophenyl)ethyl, 2-(3-methylthiophenyl)ethyl, 2-(4-methylthiophenyl)ethyl, 2-(2-trifluoromethoxyphenyl)ethyl, 2-(3-trifluoromethoxyphenyl)ethyl, 2-(4-trifluoromethoxyphenyl)ethyl, 2-(2-nitrophenyl)ethyl, 2-(3-nitrophenyl)ethyl, 2-(4-nitrophenyl)ethyl, 2-(2-cyanophenyl)ethyl, 2-(3-cyanophenyl)ethyl, 2-(4-cyanophenyl)ethyl, 2-(2-fluorophenyl)ethyl, 2-(3-fluorophenyl)ethyl, 2-(4-fluorophenyl)ethyl, 2-(3,4-difluorophenyl)ethyl, 2-(3,5-difluorophenyl)ethyl, 2-(2,6-difluorophenyl)ethyl, 2-(2,4-difluorophenyl)ethyl, 2-(2-chlorophenyl)ethyl, 2-(3-chlorophenyl)ethyl, 2-(4-chlorophenyl)ethyl, 2-(3,4-dichlorophenyl)ethyl, 2-(3,5-dichlorophenyl)ethyl, 2-(2,6-dichlorophenyl)ethyl, 2-(2,4-dichlorophenyl)ethyl, 2-(2-bromophenyl)ethyl, 2-(3-bromophenyl)ethyl, 2-(4-bromophenyl)ethyl, 2-(3,4-dibromophenyl)ethyl, 2-(3,5-dibromophenyl)ethyl, 2-(2,6-dibromophenyl)ethyl, 2-(2,4-dibromophenyl)ethyl and the like.

The phenoxy C1-C2 alkyl in which pheoxy may be substituted, represented by R1, includes C1-C2 alkyl substituted with phenoxy which may be substituted with one or more selected from the substitution group A. More specifically it includes phenyloxymethyl, 1-(phenyloxy)ethyl, 2-(phenyloxy)ethyl, (2-methylphenyl)oxymethyl, (3-methylphenyl)oxymethyl, (4-methylphenyl)oxymethyl, (2-trifluoromethylphenyl)oxymethyl, (3-trifluoromethylphenyl)oxymethyl, (4-trifluoromethylphenyl)oxymethyl, (2-methoxyphenyl)oxymethyl, (3-methoxyphenyl)oxymethyl, (4-methoxyphenyl)oxymethyl, (2-methylthiophenyl)oxymethyl, (3-methylthiophenyl)oxymethyl, (4-methylthiophenyl)oxymethyl, (2-trifluoromethoxyphenyl)oxymethyl, (3-trifluoromethoxyphenyl)oxymethyl, (4-trifluoromethoxyphenyl)oxymethyl, (2-nitrophenyl)oxymethyl, (3-nitrophenyl)oxymethyl, (4-nitrophenyl)oxymethyl, (2-cyanophenyl)oxymethyl, (3-cyanophenyl)oxymethyl, (4-cyanophenyl)oxymethyl, (2-fluorophenyl)oxymethyl, (3-fluorophenyl)oxymethyl, (4-fluorophenyl)oxymethyl, (3,4-difluorophenyl)oxymethyl, (3,5-difluorophenyl)oxymethyl, (2,6-difluorophenyl)oxymethyl, (2,4-difluorophenyl)oxymethyl, (2-chlorophenyl)oxymethyl, (3-chlorophenyl)oxymethyl, (4-chlorophenyl)oxymethyl, (3,4-dichlorophenyl)oxymethyl, (3,5-dichlorophenyl)oxymethyl, (2,6-dichlorophenyl)oxymethyl, (2,4-dichlorophenyl)oxymethyl, (2-bromophenyl)oxymethyl, (3-bromophenyl)oxymethyl, (4-bromophenyl)oxymethyl, (3,4-dibromophenyl)oxymethyl, (3,5-dibromophenyl)oxymethyl, (2,6-dibromophenyl)oxymethyl, (2,4-dibromophenyl)oxymethyl and the like.

The phenyl C2-C3 alkoxyalkyl in which phenyl may be substituted, represented by R1, includes C2-C3 alkoxyalkyl substituted with phenyl which may be substituted with one or more selected from the substitution group A. More specifically it includes benzyloxymethyl (2-methylbenzyl)oxymethyl, (3-methylbenzyl)oxymethyl, (4-methylbenzyl)oxymethyl, (2-trifluoromethylbenzyl)oxymethyl, (3-trifluoromethylbenzyl)oxymethyl, (4-trifluoromethylbenzyl)oxymethyl, (2-methoxybenzyl)oxymethyl, (3-methoxybenzyl)oxymethyl, (4-methoxybenzyl)oxymethyl, (2-methylthiobenzyl)oxymethyl, (3-methylthiobenzyl)oxymethyl, (4-methylthiobenzyl)oxymethyl, (2-trifluoromethoxybenzyl)oxymethyl, (3-trifluoromethoxybenzyl)oxymethyl, (4-trifluoromethoxybenzyl)oxymethyl, (2-nitrobenzyl)oxymethyl, (3-nitrobenzyl)oxymethyl, (4-nitrobenzyl)oxymethyl, (2-cyanobenzyl)oxymethyl, (3-cyanobenzyl)oxymethyl, (4-cyanobenzyl)oxymethyl, (2-fluorobenzyl)oxymethyl, (3-fluorobenzyl)oxymethyl, (4-fluorobenzyl)oxymethyl, (3,4-difluorobenzyl)oxymethyl, (3,5-difluorobenzyl)oxymethyl, (2,6-difluorobenzyl)oxymethyl, (2,4-difluorobenzyl)oxymethyl, (2-chlorobenzyl)oxymethyl, (3-chlorobenzyl)oxymethyl, (4-chlorobenzyl)oxymethyl, (3,4-dichlorobenzyl)oxymethyl, (3,5-dichlorobenzyl)oxymethyl, (2,6-dichlorobenzyl)oxymethyl, (2,4-dichlorobenzyl)oxymethyl, (2-bromobenzyl)oxymethyl, (3-bromobenzyl)oxymethyl, (4-bromobenzyl)oxymethyl, (3,4-dibromobenzyl)oxymethyl, (3,5-dibromobenzyl)oxymethyl, (2,6-dibromobenzyl)oxymethyl, (2,4-dibromobenzyl)oxymethyl and the like.

The substituent of the formula (B), represented by R1, includes the substituent wherein $R^3$ is C1-C3 alkyl and $R^4$ is a hydrogen atom, the substituent wherein $R^3$ is C1-C3 alkyl and $R^4$ is phenyl which may be substituted with one or more selected from the substitution group A, and the like; more specifically, acetoxymethyl, α-acetyloxybenzyl and the like.

The phenyl C1-C4 alkyl in which phenyl may be substitued, represented by R2, includes C1-C4 alkyl substituted with phenyl which may be substituted with one or more selected from the substitution group A; more specifically, benzyl, 4-halogenobenzyl, 3-halogenobenzyl, 4-trifluoromethylbenzyl, 3-trifluoromethylbenzyl, 4-trifluoromethoxybenzyl, 3-trifluoromethoxybenzyl, 3,4-dihalogenobenzyl, 3,5-dihalogenobenzyl, 2,6-dihalogenobenzyl, 1-phenylethyl, 1-(fluorophenyl)ethyl, 1-(chlorophenyl)ethyl, 1-phenylpropyl, 2-phenylethyl, 2-(fluorophenyl)ethyl, 2-(chlorophenyl)ethyl, 3-phenylpropyl and the like.

The pyridyl C1-C4 alkyl in which pyridyl may be substituted, represented by R2, includes C1-C4 alkyl substituted with 2-pyridyl, 3-pyridyl or 4-pyridyl which may be substituted with one or more selected from the substitution group A; more specifically, (2-pyridyl)methyl, (3-pyridyl)methyl, (4-pyridyl)methyl, 1-(2-pyridyl)ethyl, 1-(3-pyridyl)ethyl, 1-(4-pyridyl)ethyl, 2-(2-pyridyl)ethyl, 2-(3-pyridyl)ethyl, 2-(4-pyridyl)ethyl, (6-chloro-2-pyridyl)methyl and the like.

The pyrimidyl C1-C4 alkyl in which pyrimidyl may be substituted, represented by R2, includes C1-C4 alkyl substituted with 2-pyrimidyl, 4-pyrimidyl or 5-pyrimidyl which may be substituted with one or more selected from the substitution group A; more specifically, (2-pyrimidyl)methyl, (4-pyrimidyl)methyl, (5-pyrimidyl)methyl and the like.

Embodiments of the present compound include, for example, the following compounds:

the thiadiazole compound wherein $R^1$ is methyl in the formula (A);

the thiadiazole compound wherein $R^1$ is C3-C7 alkenyl, C2-C7 alkoxyalkyl, C2-C7 alkylthioalkyl, C4-C7 alkoxyalkoxyalkyl or C4-C7 alkylthioalkoxyalkyl in the formula (A);

the thiadiazole compound wherein $R^1$ is the C3-C7 alkenyl which has double bond at the 2-position in the formula (A);

the thiadiazole compound wherein $R^1$ is allyl in the formula (A);

the thiadiazole compound wherein $R^1$ is (C1-C6 alkoxy)methyl or (C1-C6 alkylthio)methyl in the formula (A);

the thiadiazole compound wherein $R^1$ is methoxymethyl in the formula (A);

the thiadiazole compound wherein $R^1$ is ethoxymethyl in the formula (A);

the thiadiazole compound wherein $R^1$ is methoxyethoxymethyl in the formula (A);

the thiadiazole compound wherein $R^1$ is phenyl C1-C2 alkyl in which phenyl may be substituted with one or more selected from the substitution group A, phenyloxy C1-C2 alkyl in which phenyloxy may be substituted with one or more selected from the substitution group A, or phenyl C2-C3 alkoxyalkyl in which phenyl may be substituted with one or more selected from the substitution group A in the formula (A);

the thiadiazole compound wherein $R^1$ is benzyl which may be substituted with one or more selected from the substitution group A, phenyloxymethyl which may be substituted with one or more selected from the substitution group A, or benzyloxymethyl which may be substituted with one or more selected from the substitution group A in the formula (A);

the thiadiazole compound wherein $R^1$ is benzyl in the formula (A);

the thiadiazole compound wherein $R^1$ is benzyl substituted with (a) halogen atom(s) in the formula (A);

the thiadiazole compound wherein $R^1$ is benzyl substituted with (a) fluorine atom(s) in the formula (A);

the thiadiazole compound wherein $R^1$ is benzyl substituted with (a) chlorine atom(s) in the formula (A);

the thiadiazole compound wherein $R^1$ is benzyl substituted with methyl in the formula (A);

the thiadiazole compound wherein $R^1$ is benzyl substituted with methoxy in the formula (A);

the thiadiazole compound wherein $R^1$ is benzyl substituted with trifluoromethyls at one or two places in the formula (A);

the thiadiazole compound wherein $R^1$ is benzyl substituted with trifluoromethoxy at one place in the formula (A);

the thiadiazole compound wherein $R^1$ is benzyloxymethyl in the formula (A);

the thiadiazole compound wherein $R^1$ is acetoxymethyl in the formula (A);

the thiadiazole compound wherein $R^2$ is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein $R^2$ is phenyl C1-C4 alkyl in which the phenyl may be substituted with one or more selected from the group (hereinafter, referred to as the substitution group B) consisting of C1-C4 alkyl, C1-C4 haloalkyl, C1-C4 alkoxy, C1-C4 alkylthio, C1-C4 haloalkoxy and halogen atoms, pyridyl C1-C4 alkyl in which the pyridyl may be substituted with one or more selected from the substitution group B, or pyrimidyl C1-C4 alkyl in which the pyrimidyl may be substituted with one or more selected from the substitution group B in the formula (A);

the thiadiazole compound wherein $R^2$ is phenyl C1-C4 alkyl in which the phenyl may be substituted with one or more selected from the substitution group B, or pyridyl C1-C4 alkyl in which the pyridyl may be substituted with one or more selected from the substitution group B in the formula (A);

the thiadiazole compound wherein $R^2$ is benzyl in the formula (A);

the thiadiazole compound wherein $R^2$ is benzyl substituted with (a) halogen atom(s) in the formula (A);

the thiadiazole compound wherein $R^2$ is benzyl substituted with (a) fluorine atom(s) in the formula (A);

the thiadiazole compound wherein $R^2$ is benzyl substituted with (a) chlorine atom(s) in the formula (A);

the thiadiazole compound wherein $R^2$ is benzyl substituted with (a) bromine atom(s) in the formula (A);

the thiadiazole compound wherein $R^2$ is benzyl substituted with (a) iodine atom(s) in the formula (A);

the thiadiazole compound wherein $R^2$ is benzyl substituted with methyl in the formula (A);

the thiadiazole compound wherein $R^2$ is benzyl substituted with trifluoromethyls at one or two places in the formula (A);

the thiadiazole compound wherein $R^2$ is benzyl substituted with trifluoromethoxy at one place in the formula (A);

the thiadiazole compound wherein $R^2$ is 1-phenylethyl in the formula (A);

the thiadiazole compound wherein $R^2$ is 1-phenylethyl in which the phenyl is substituted with a fluorine atom or a chlorine atom at one place in the formula (A);

the thiadiazole compound wherein $R^2$ is 1-phenylpropyl in the formula (A);

the thiadiazole compound wherein $R^2$ is 2-phenylethyl in which the phenyl is substituted with a fluorine atom or chlorine atom at one place in the formula (A);

the thiadiazole compound wherein $R^2$ is 3-phenylpropyl in the formula (A);

the thiadiazole compound wherein $R^2$ is pyridylmethyl in the formula (A);

the thiadiazole compound wherein $R^2$ is pyridylmethyl in which the pyridyl is substituted with a fluorine atom at one place in the formula (A);

the thiadiazole compound wherein $R^2$ is pyridylmethyl in which the pyridyl is substituted with a chlorine atom at one place in the formula (A);

the thiadiazole compound wherein $R^2$ is 2-pyridylmethyl substituted with a fluorine or chlorine atom at 6-position in the formula (A);

the thiadiazole compound wherein $R^2$ is 2-(2-pyridyl)ethyl in the formula (A);

the thiadiazole compound wherein $R^2$ is 2-(3-pyridyl)ethyl in the formula (A);

the thiadiazole compound wherein $R^2$ is 2-(4-pyridyl)ethyl in the formula (A);

the thiadiazole compound wherein $R^2$ is pyrimidylmethyl in the formula (A);

the thiadiazole compound wherein $R^2$ is 2-pyrimidylmethyl in the formula (A);

the thiadiazole compound wherein $R^2$ is 4-pyrimidylmethyl in the formula (A);

the thiadiazole compound wherein $R^2$ is 5-pyrimidylmethyl in the formula (A);

the thiadiazole compound wherein $R^1$ is methyl, and $R^2$ is phenyl C1-C4 alkyl in which the phenyl may be substituted, pyridyl C1-C4 alkyl in which the pyridyl may be substituted, or pyrimidyl C1-C4 alkyl in which the pyrimidyl may be substituted in the formula (A);

the thiadiazole compound wherein $R^1$ is methyl, and $R^2$ is phenyl C1-C4 alkyl in which the phenyl may be substituted, or pyridyl C1-C4 alkyl in which the pyridyl may be substituted in the formula (A);

the thiadiazole compound wherein $R^1$ is methyl, and $R^2$ is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein R¹ is methyl, and R² is phenyl C1-C4 alkyl in which the phenyl may be substituted with one or more selected from the substitution group A, or pyridyl C1-C4 alkyl in which the pyridyl may be substituted with one or more selected from the substitution group A in the formula (A);

the thiadiazole compound wherein R¹ is C3-C7 alkenyl, C2-C7 alkoxyalkyl, C2-C7 alkylthioalkyl, C4-C7 alkoxyalkoxyalkyl or C4-C7 alkylthioalkoxyalkyl, and R² is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein R¹ is phenyl C1-C2 alkyl in which phenyl may be substituted with one or more selected from the substitution group A, phenyloxy C1-C2 alkyl in which phenyloxy may be substituted with one or more selected from the substitution group A, or phenyl C2-C3 alkoxyalkyl in which phenyl may be substituted with one or more selected from the substitution group A, and R² is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein R¹ is (C1-C6 alkoxy)methyl or (C1-C6 alkylthi)methyl, and R² is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein R¹ is benzyl which may be substituted with one or more selected from the substitution group A, phenyloxymethyl which may be substituted with one or more selected from the substitution group A, or benzyloxymethyl which may be substituted with one or more selected from the substitution group A, and R² is phenyl C1-C4 alkyl in which the phenyl may be substituted with one or more selected from the substitution group A, pyridyl C1-C4 alkyl in which the pyridyl may be substituted with one or more selected from the substitution group A, or pyrimidyl C1-C4 alkyl in which the pyrimidyl may be substituted with one or more selected from the substitution group A in the formula (A);

the thiadiazole compound wherein R¹ is methyl, and R² is benzyl which may be substituted with (a) halogen atom(s) in the formula (A);

the thiadiazole compound wherein R¹ is C3-C7 alkenyl, C2-C7 alkoxyalkyl, C2-C7 alkylthioalkyl, C4-C7 alkoxyalkoxyalkyl, or C4-C7 alkylthioalkoxyalkyl, and R² is benzyl substituted with a halogen atom in the formula (A);

the thiadiazole compound wherein R¹ is benzyl which may be substituted with one or more selected from the substitution group A, phenyloxymethyl which may be substituted with one or more selected from the substitution group A, or benzyloxymethyl which may be substituted with one or more selected from the substitution group A, and R² is benzyl substituted with a halogen atom in the formula (A);

the thiadiazole compound wherein R¹ is benzyl, and R² is benzyl substituted with a halogen atom in the formula (A).

The following will describe a production process for the present compounds.

In the present compound, the compound wherein R¹ is methy, C3-C7 alkenyl, C2-C7 alkoxyalkyl, C2-C7 alkylthioalkyl, C4-C7 alkoxyalkoxyalkyl, C4-C7 alkylthioalkoxyalkyl, phenyl C1-C2 alkyl in which phenyl may be substituted, phenyloxy C1-C2 alkyl in which phenyloxy may be substituted, phenyl C2-C3 alkoxyalkyl in which phenyl may be substituted, namely the compound of the formula (A-1), can be produced, for example, by making a 5-chloro-1,2,4-thiadiazole compound of the formula (I) react with an alcohol compound of the formula (II).

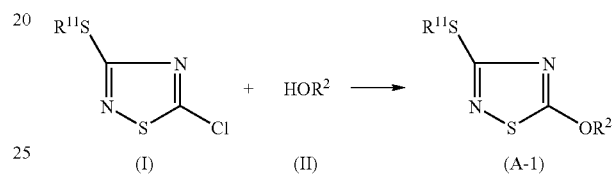

wherein R¹¹ is methy, C3-C7 alkenyl, C2-C7 alkoxyalkyl, C2-C7 alkylthioalkyl, C4-C7 alkoxyalkoxyalkyl, C4-C7 alkylthioalkoxyalkyl, phenyl C1-C2 alkyl in which phenyl may be substituted, phenyloxy C1-C2 alkyl in which phenyloxy may be substituted, phenyl C2-C3 alkoxyalkyl in which phenyl may be substituted, and R² has the same meaning as described above.

The reaction is generally carried out in the presence of base in a solvent. The solvent to be used in the reaction includes, for example, aliphatic hydrocarbons such as hexane, heptane, octane and the like; aromatic hydrocarbons such as toluene, xylene and the like; ethers such as tetrahydrofuran, 1,4-dioxane, methyl tert-butyl ether, 1,2-dimethoxyethane and the like; acid amides such as N,N-dimethylformamide and the like, and mixtures thereof. The base to be used in the reaction includes, for example, inorganic base such as sodium hydride, potassium carbonate and the like. Concerning the amount of the reagents, the amount of the alcohol compound of the formula (II) is usually 1 to 1.5 mole based on 1 mole of the 5-chloro-1,2,4-thiadiazole compound of the formula (I), and the amount of the base is usually 1 to 1.5 mole based on 1 mole of the alcohol compound of the formula (II). The reaction temperature is usually in the range of −20° C. to 80° C., and the reaction time is usually in the range of 0.5 to 24 hours.

After completion of the reaction, the present compound of the formula (A-1) can be isolated by subjecting the reaction mixture to post-treatment such as adding the reaction mixture into water, extracting with an organic solvent, drying and concentrating the organic phase obtained and the like. The isolated present compound of the formula (A-1) can be purified by a technique such as chromatography, recrystallization and the like, if necessary.

In the present compound, the compound wherein R¹ is the group of the formula (B), namely the compound of the formula (A-2), can be produced, for example, by making the thiadiazole compound of the formula (III) react with an oxidizing reagent to obtain the sulfoxide compound of the formula (IV) (hereinafter, referred to as Step 1), and making the sulfoxide compound of the formula (IV) react with the acid anhydride of the formula (V) (hereinafter, referred to as Step 2).

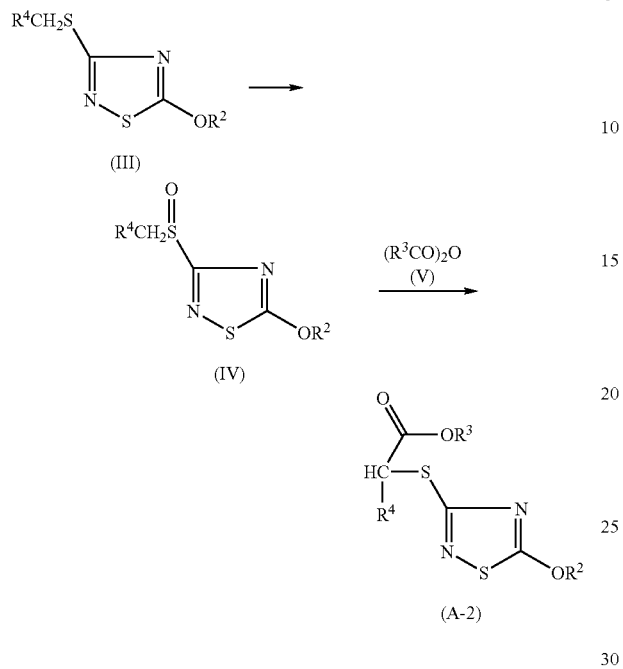

(III)

(IV)

(A-2)

wherein $R^2$, $R^3$ and $R^4$ have the same meaning as described above.

Step 1

The reaction is generally carried out in a solvent. The solvent to be used in the reaction includes, for example, halogenated aliphatic hydrocarbons such as dichloromethane, chloroform and the like.

The oxidizing reagent to be used in the reaction includes, for example, peracid such as 2-chloro perbenzoic acid and the like. The amount of the oxidizing reagent to be used in the reaction is usually 1 to 1.5 mole based on 1 mole of the thiadiazole compound of the formula (III). The reaction temperature is usually in the range of −20° C. to 30° C., and the reaction time is usually in the range of momentary to 24 hours.

After completion of the reaction, the sulfoxide compound of the formula (IV) can be isolated by subjecting the reaction mixture to post-treatment such as adding the reaction mixture into water, extracting with an organic solvent, if necessary washing the organic phase with an aqueous solution of reducing reagent such as sodium sulfite, sodium thiosulfate and the like, drying and concentrating the organic phase obtained and the like. The isolated sulfoxide compound of the formula (IV) can be purified by a technique such as chromatography, recrystallization and the like.

Step 2

The reaction is carried out by making the sulfoxide compound of the formula (IV) react with the acid anhydride of the formula (V), and generally carried out in the presence of base, and may be carried out in a solvent. The base to be used in the reaction includes, for example, pyridines such as 2,6-lutidine and the like, and alkali metal salt of acetic acid such as sodium acetate and the like.

Concerning the amount of the reagents, the amount of the acid anhydride of the formula (V) is usually 1 to 50 moles and the amount of the base is 1 to 10 moles, based on 1 mole of the sulfoxide compound of the formula (IV).

The reaction temperature is usually in the range of 0° C. to 150° C., and the reaction time is usually in the range of 1 to 72 hours.

After completion of the reaction, the present compound of the formula (A-2) can be isolated by subjecting the reaction mixture to post-treatment such as adding the reaction mixture into an aqueous solution of sodium hydrogen carbonate and the like, extracting with an organic solvent, drying and concentrating the organic phase obtained and the like. The isolated present compound of the formula (A-2) can be purified by a technique such as chromatography, recrystallization and the like.

The compound of the formula (I) can be produced, for example, by the method described in Chem. Ber. 90, 892 (1957).

Next, examples of the present compound are shown.

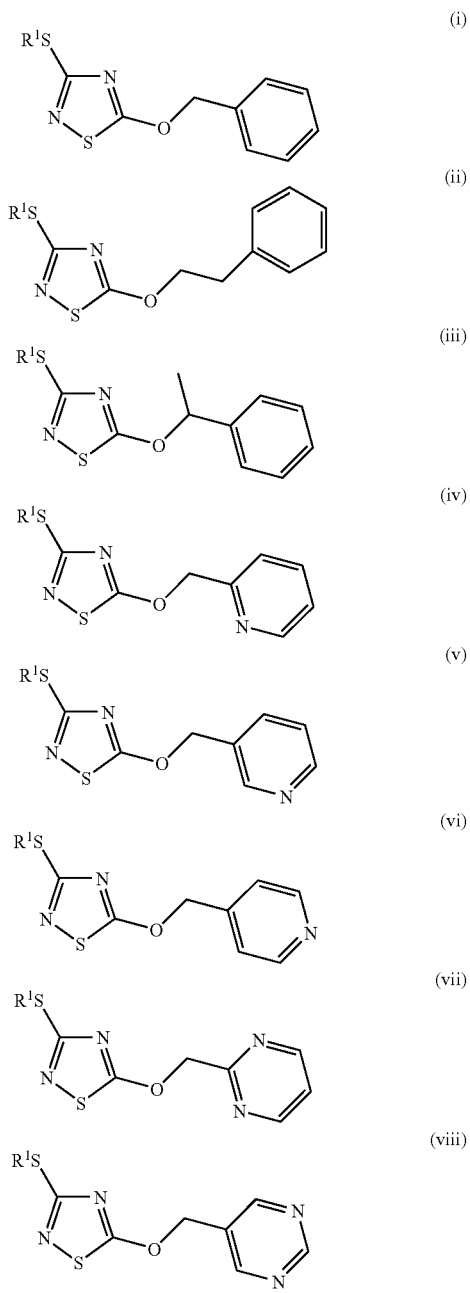

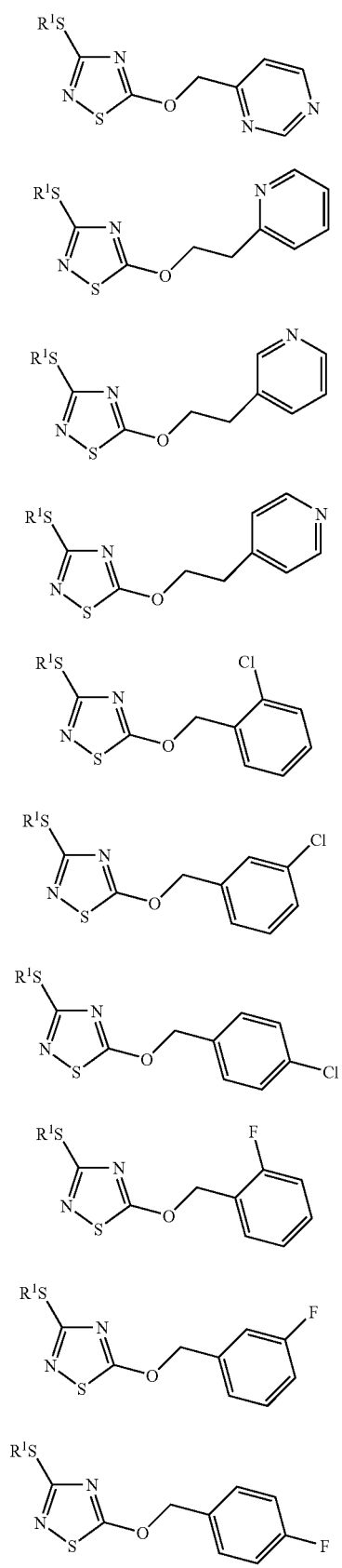
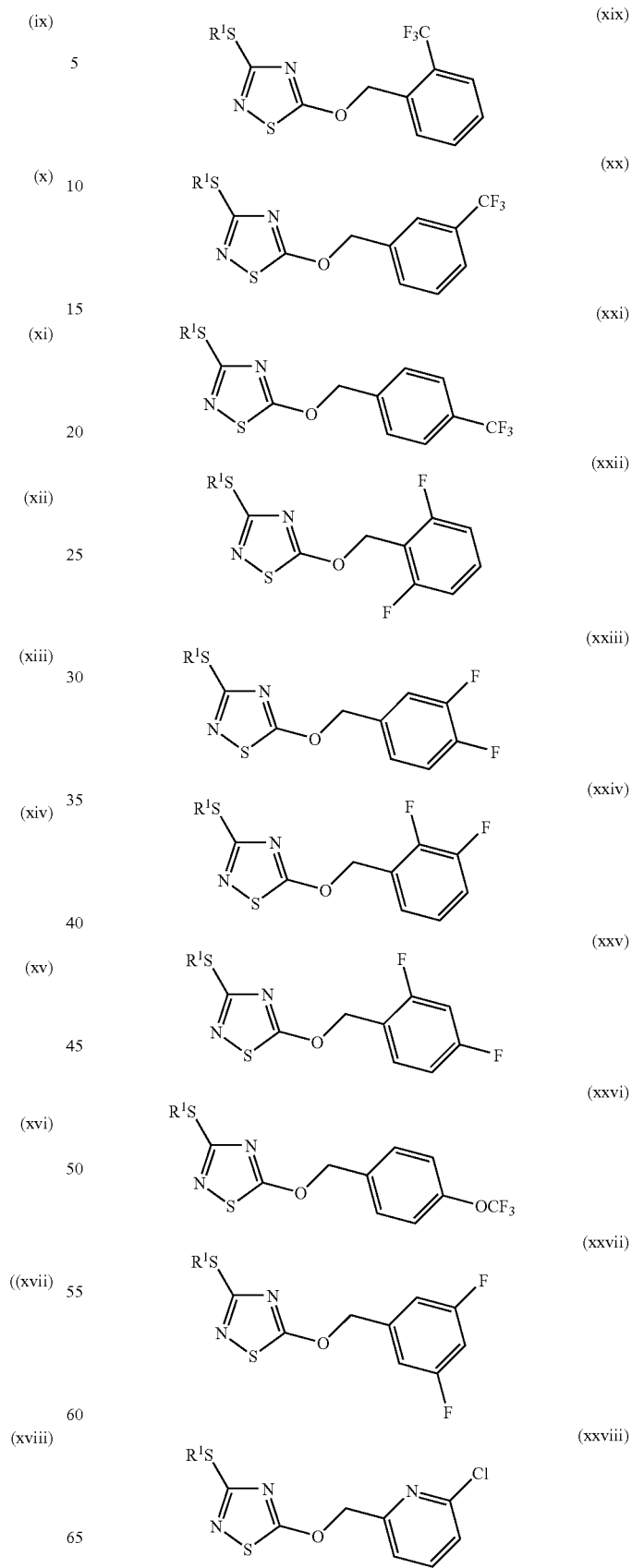

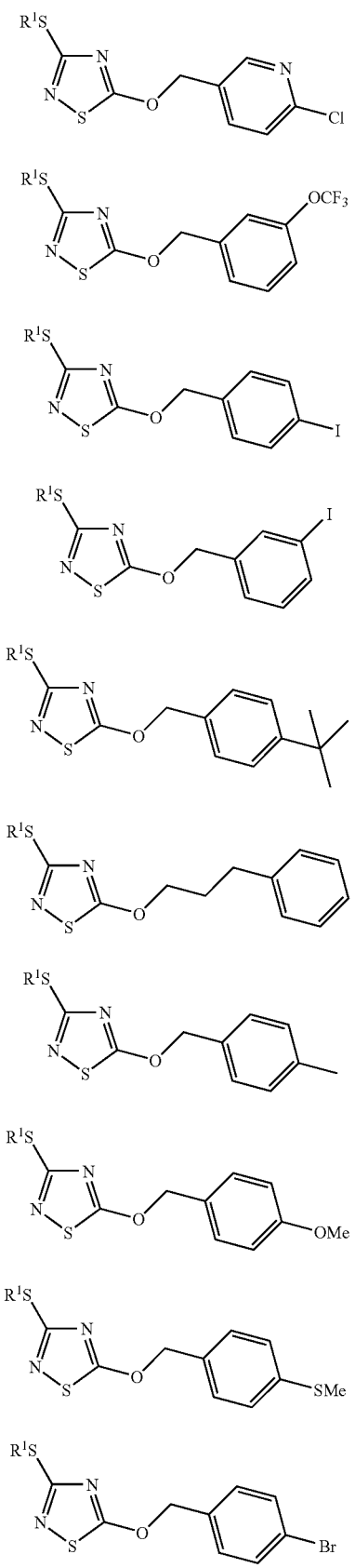
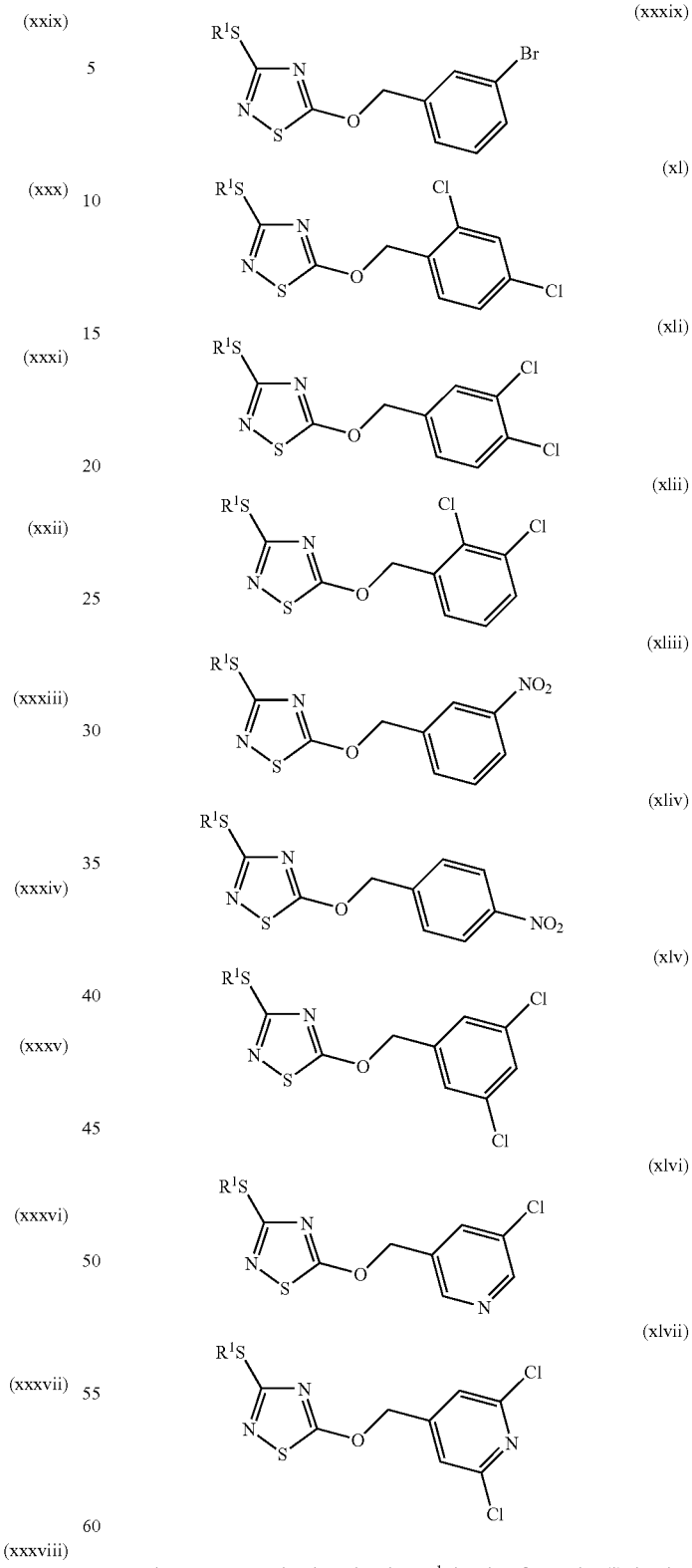
The compound wherein the R[1] in the formula (i) is the substituent described below.
Methyl; allyl, 2-butenyl, 3-methyl-2-butenyl, 2-pentenyl; methoxymethyl, ethoxymethyl, propoxymethyl, isopropoxymethyl, butoxymethyl, isobutoxymethyl, sec-butoxymethyl, tert-butoxymethyl; methylthiomethyl, ethylthiomethyl, propylthiomethyl, isopropylthiomethyl; (methoxyethoxy)methyl, (ethoxyethoxy)methyl; (methylthioethoxy)methyl; benzyl, 2-methylbenzyl, 3-methylbenzyl, 4-methylbenzyl, 2-trifluoromethylbenzyl, 3-trifluoromethylbenzyl, 4-trifluoromethylbenzyl, 2-methoxybenzyl, 3-methoxybenzyl, 4-methoxybenzyl, 2-methylthiobenzyl, 3-methylthiobenzyl, 4-methylthiobenzyl, 2-trifluoromethoxybenzyl, 3-trifluoromethoxybenzyl, 4-trifluoromethoxybenzyl, 2-nitrobenzyl, 3-nitrobenzyl, 4-nitrobenzyl, 2-cyanobenzyl, 3-cyanobenzyl, 4-cyanobenzyl, 2-fluorobenzyl, 3-fluorobenzyl, 4-fluorobenzyl, 3,4-difluorobenzyl, 3,5-difluorobenzyl, 2,6-difluorobenzyl, 2,4-difluorobenzyl, 2-chlorobenzyl, 3-chlorobenzyl, 4-chlorobenzyl, 3,4-dichlorobenzyl, 3,5-dichlorobenzyl, 2,6-dichlorobenzyl, 2,4-dichlorobenzyl, 2-bromobenzyl, 3-bromobenzyl, 4-bromobenzyl, 3,4-dibromobenzyl, 3,5-dibromobenzyl, 2,6-dibromobenzyl, 2,4-dibromobenzyl, 1-phenylethyl, 1-(2-methylphenyl)ethyl, 1-(3-methylphenyl)ethyl, 1-(4-methylphenyl)ethyl, 1-(2-trifluoromethylphenyl)ethyl, 1-(3-trifluoromethylphenyl)ethyl, 1-(4-trifluoromethylphenyl)ethyl, 1-(2-methoxyphenyl)ethyl, 1-(3-methoxyphenyl)ethyl, 1-(4-methoxyphenyl)ethyl, 1-(2-methylthiophenyl)ethyl, 1-(3-methylthiophenyl)ethyl, 1-(4-methylthiophenyl)ethyl, 1-(2-trifluoromethoxyphenyl)ethyl, 1-(3-trifluoromethoxyphenyl)ethyl, 1-(4-trifluoromethoxyphenyl)ethyl, 1-(2-nitrophenyl)ethyl, 1-(3-nitrophenyl)ethyl, 1-(4-nitrophenyl)ethyl, 1-(2-cyanophenyl)ethyl, 1-(3-cyanophenyl)ethyl, 1-(4-cyanophenyl)ethyl, 1-(2-fluorophenyl)ethyl, 1-(3-fluorophenyl)ethyl, 1-(4-fluorophenyl)ethyl, 1-(3,4-difluorophenyl)ethyl, 1-(3,5-difluorophenyl)ethyl, 1-(2,6-difluorophenyl)ethyl, 1-(2,4-difluorophenyl)ethyl, 1-(2-chlorophenyl)ethyl, 1-(3-chlorophenyl)ethyl, 1-(4-chlorophenyl)ethyl, 1-(3,4-dichlorophenyl)ethyl, 1-(3,5-dichlorophenyl)ethyl, 1-(2,6-dichlorophenyl)ethyl, 1-(2,4-dichlorophenyl)ethyl, 1-(2-bromophenyl)ethyl, 1-(3-bromophenyl)ethyl, 1-(4-bromophenyl)ethyl, 1-(3,4-dibromophenyl)ethyl, 1-(3,5-dibromophenyl)ethyl, 1-(2,6-dibromophenyl)ethyl, 1-(2,4-dibromophenyl)ethyl, 2-phenylethyl, 2-(2-methylphenyl)ethyl, 2-(3-methylphenyl)ethyl, 2-(4-methylphenyl)ethyl, 2-(2-trifluoromethylphenyl)ethyl, 2-(3-trifluoromethylphenyl)ethyl, 2-(4-trifluoromethylphenyl)ethyl, 2-(2-methoxyphenyl)ethyl, 2-(3-methoxyphenyl)ethyl, 2-(4-methoxyphenyl)ethyl, 2-(2-methylthiophenyl)ethyl 2-(3-methylthiophenyl)ethyl, 2-(4-methylthiophenyl)ethyl, 2-(2-trifluoromethoxyphenyl)ethyl, 2-(3-trifluoromethoxyphenyl)ethyl, 2-(4-trifluoromethoxyphenyl)ethyl, 2-(2-nitrophenyl)ethyl, 2-(3-nitrophenyl)ethyl, 2-(4-nitrophenyl)ethyl, 2-(2-cyanophenyl)ethyl, 2-(3-cyanophenyl)ethyl, 2-(4-cyanophenyl)ethyl, 2-(2-fluorophenyl)ethyl, 2-(3-fluorophenyl)ethyl, 2-(4-fluorophenyl)ethyl, 2-(3,4-difluorophenyl)ethyl, 2-(3,5-difluorophenyl)ethyl, 2-(2,6-difluorophenyl)ethyl, 2-(2,4-difluorophenyl)ethyl, 2-(2-chlorophenyl)ethyl, 2-(3-chlorophenyl)ethyl, 2-(4-chlorophenyl)ethyl, 2-(3,4-dichlorophenyl)ethyl, 2-(3,5-dichlorophenyl)ethyl, 2-(2,6-dichlorophenyl)ethyl, 2-(2,4-dichlorophenyl)ethyl, 2-(2-bromophenyl)ethyl, 2-(3-bromophenyl)ethyl, 2-(4-bromophenyl)ethyl, 2-(3,4-dibromo phenyl)ethyl, 2-(3,5-dibromophenyl)ethyl, 2-(2,6-dibromophenyl)ethyl, 2-(2,4-dibromophenyl)ethyl; phenyloxymethyl, 1-(phenyloxy)ethyl, 2-(phenyloxy)ethyl (2-methylphenyl)oxymethyl, (3-methylphenyl)oxymethyl, (4-methylphenyl)oxymethyl, (2-trifluoromethylphenyl)oxymethyl, (3-trifluoromethylphenyl)oxymethyl, (4-trifluoromethylphenyl)oxymethyl, (2-methoxyphenyl)oxymethyl, (3-methoxyphenyl)oxymethyl, (4-methoxyphenyl)oxymethyl, (2-methylthiophenyl)oxymethyl, (3-methylthiophenyl)oxymethyl, (4-methylthiophenyl)oxymethyl, (2-trifluoromethoxyphenyl)oxymethyl, (3-trifluoromethoxyphenyl)oxymethyl, (4-trifluoromethoxyphenyl)oxymethyl, (2-nitrophenyl)oxymethyl, (3-nitrophenyl)oxymethyl, (4-nitrophenyl)oxymethyl, (2-cyanophenyl)oxymethyl, (3-cyanophenyl)oxymethyl, (4-cyanophenyl)oxymethyl, (2-fluorophenyl)oxymethyl, (3-fluorophenyl)oxymethyl, (4-fluorophenyl)oxymethyl, (3,4-difluorophenyl)oxymethyl, (3,5-difluorophenyl)oxymethyl, (2,6-difluorophenyl)oxymethyl, (2,4-difluorophenyl)oxymethyl, (2-chlorophenyl)oxymethyl, (3-chlorophenyl)oxymethyl, (4-chlorophenyl)oxymethyl, (3,4-dichlorophenyl)oxymethyl, (3,5-dichlorophenyl)oxymethyl, (2,6-dichlorophenyl)oxymethyl, (2,4-dichlorophenyl)oxymethyl, (2-bromophenyl)oxymethyl, (3-bromophenyl)oxymethyl, (4-bromophenyl)oxymethyl, (3,4-dibromophenyl)oxymethyl, (3,5-dibromophenyl)oxymethyl, (2,6-dibromophenyl)oxymethyl, (2,4-dibromophenyl)oxymethyl; benzyloxymethyl, (2-methylbenzyl)oxymethyl, (3-methylbenzyl)oxymethyl, (4-methylbenzyl)oxymethyl, (2-trifluoromethylbenzyl)oxymethyl, (3-trifluoromethylbenzyl)oxymethyl, (4-trifluoromethylbenzyl)oxymethyl, (2-methoxybenzyl)oxymethyl, (3-methoxybenzyl)oxymethyl, (4-methoxybenzyl)oxymethyl, (2-methylthiobenzyl)oxymethyl, (3-methylthiobenzyl)oxymethyl, (4-methylthiobenzyl)oxymethyl, (2-trifluoromethoxybenzyl)oxymethyl, (3-trifluoromethoxybenzyl)oxymethyl, (4-trifluoromethoxybenzyl)oxymethyl, (2-nitrobenzyl)oxymethyl, (3-nitrobenzyl)oxymethyl, (4-nitrobenzyl)oxymethyl, (2-cyanobenzyl)oxymethyl, (3-cyanobenzyl)oxymethyl, (4-cyanobenzyl)oxymethyl, (2-fluorobenzyl)oxymethyl, (3-fluorobenzyl)oxymethyl, (4-fluorobenzyl)oxymethyl, (3,4-difluorobenzyl)oxymethyl, (3,5-difluorobenzyl)oxymethyl, (2,6-difluorobenzyl)oxymethyl, (2,4-difluorobenzyl)oxymethyl, (2-chlorobenzyl)oxymethyl, (3-chlorobenzyl)oxymethyl, (4-chlorobenzyl)oxymethyl, (3,4-dichlorobenzyl)oxymethyl, (3,5-dichlorobenzyl)oxymethyl, (2,6-dichlorobenzyl)oxymethyl, (2,4-dichlorobenzyl)oxymethyl, (2-bromobenzyl)oxymethyl, (3-bromobenzyl)oxymethyl, (4-bromobenzyl)oxymethyl, (3,4-dibromobenzyl)oxymethyl, (3,5-dibromobenzyl)oxymethyl, (2,6-dibromobenzyl)oxymethyl, (2,4-dibromobenzyl)oxymethyl; acetyloxymethyl, propionyloxymethyl, α-acetoxybenzyl.

The compound wherein the $R^1$ in the formula (ii) is the substituent described above.

The compound wherein the $R^1$ in the formula (ii) is the substituent described above.

The compound wherein the $R^1$ in the formula (iii) is the substituent described above.

The compound wherein the $R^1$ in the formula (iv) is the substituent described above.

The compound wherein the $R^1$ in the formula (v) is the substituent described above.

The compound wherein the $R^1$ in the formula (vi) is the substituent described above.

The compound wherein the $R^1$ in the formula (vii) is the substituent described above.

The compound wherein the $R^1$ in the formula (viii) is the substituent described above.

The compound wherein the $R^1$ in the formula (ix) is the substituent described above.

The compound wherein the $R^1$ in the formula (x) is the substituent described above.

The compound wherein the $R^1$ in the formula (xi) is the substituent described above.

The compound wherein the $R^1$ in the formula (xii) is the substituent described above.

The compound wherein the $R^1$ in the formula (xiii) is the substituent described above.

The compound wherein the $R^1$ in the formula (xiv) is the substituent described above.

The compound wherein the $R^1$ in the formula (xv) is the substituent described above.

The compound wherein the $R^1$ in the formula (xvi) is the substituent described above.

The compound wherein the $R^1$ in the formula (xvii) is the substituent described above.

The compound wherein the $R^1$ in the formula (xviii) is the substituent described above.

The compound wherein the $R^1$ in the formula (xix) is the substituent described above.

The compound wherein the $R^1$ in the formula (xx) is the substituent described above.

The compound wherein the $R^1$ in the formula (xxi) is the substituent described above.

The compound wherein the $R^1$ in the formula (xxii) is the substituent described above.

The compound wherein the $R^1$ in the formula (xxiii) is the substituent described above.

The compound wherein the $R^1$ in the formula (xxiv) is the substituent described above.

The compound wherein the $R^1$ in the formula (xxv) is the substituent described above.

The compound wherein the $R^1$ in the formula (xxvi) is the substituent described above.

The compound wherein the $R^1$ in the formula (xxvii) is the substituent described above.

The compound wherein the $R^1$ in the formula (xxviii) is the substituent described above.

The compound wherein the $R^1$ in the formula (xxix) is the substituent described above.

The compound wherein the $R^1$ in the formula (xxx) is the substituent described above.

The compound wherein the $R^1$ in the formula (xxxi) is the substituent described above.

The compound wherein the $R^1$ in the formula (xxxii) is the substituent described above.

The compound wherein the $R^1$ in the formula (xxxiii) is the substituent described above.

The compound wherein the $R^1$ in the formula (xxxiv) is the substituent described above.

The compound wherein the $R^1$ in the formula (xxxv) is the substituent described above.

The compound wherein the $R^1$ in the formula (xxxvi) is the substituent described above.

The compound wherein the $R^1$ in the formula (xxxvii) is the substituent described above.

The compound wherein the $R^1$ in the formula (xxxviii) is the substituent described above.

The compound wherein the $R^1$ in the formula (xxxix) is the substituent described above.

The compound wherein the $R^1$ in the formula (xl) is the substituent described above.

The compound wherein the $R^1$ in the formula (xli) is the substituent described above.

The compound wherein the $R^1$ in the formula (xlii) is the substituent described above.

The compound wherein the $R^1$ in the formula (xliii) is the substituent described above.

The compound wherein the $R^1$ in the formula (xliv) is the substituent described above.

The compound wherein the $R^1$ in the formula (xlv) is the substituent described above.

The compound wherein the $R^1$ in the formula (xlvi) is the substituent described above.

The compound wherein the $R^1$ in the formula (xlvii) is the substituent described above.

The arthropod pests against which the present compound has control activity may include, for example, insect pests and acarine pests. Specific examples are listed below:

Hemiptera: Delphacidae such as *Laodelphax striatellus, Nilaparvata lugens*, and *Sogatella furcifera*; Deltocephalidae such as *Nephotettix cincticeps* and *Empoasca onukii*; Aphididae such as *Aphis gossypii* and *Myzus persicae*; Pentatomidae; Aleyrodidae such as *Trialeurodes vaporariorum, Bemisia tabaci*, and *Bemisia argentifolii*; Coccidae; Tingidae; Psyllidae;

Lepidoptera: Pyralidae such as *Chilo suppressalis, Cnaphalocrocis medinalis, Ostrinia nubilalis*, and *Parapediasia teterrella*; Noctuidae such as *Spodoptera litura, Spodoptera exigua, Pseudaletia separata, Mamestra brassicae, Agrotis ipsilon, Thoricoplusia* spp., *Heliothis* spp., *Helicoverpa* spp., and *Earias* spp.; Pieridae such as *Pieris rapae crucivora*; Tortricidae such as *Adoxophyes orana fasciata, Grapholita molesta*, and *Cydia pomonella*; Carposinidae such as *Carposina niponensis*; Lyonetiidae such as *Lyonetia clerkella*; Gracillariidae such as *Phyllonorycter ringoniella*; Phyllocnistidae such as *Phyllocnistis citrella*; Yponomeutidae such as *Plutela xylostella*; Gelechiidae such as *Pectinophora gossypiella*; Arctiidae; Tineidae;

Diptera: Calicidae such as Culexpipienspallens, *Culex tritaeniorhynchus*, and *Culex quinquefasciatus; Aedes* spp. such as *Aedes aegypti* and *Aedes albopictus; Anopheles* spp. such as *Anopheles sinensis*; Chironomidae; Muscidae such as *Musca domestica* and *Muscina stabulans*; Calliphoridae; Sarcophagidae; Fanniidae; Anthomyiidae such as *Delia platura* and *Delia antiqua*; Tephritidae; Drosophilidae; Psychodidae; Tabanidae; Simuliidae; Stomoxyidae; Agromyzidae;

Coleoptera: *Diabrotica* spp. such as *Diabrotica virgifera virgifera* and *Diabrotica undecimpunctata howardi*; Scarabaeidae such as *Anomala cuprea* and *Anomala rufocuprea*; Curculionidae such as *Sitophilus zeamais, Lissorhoptrus oryzophilus*, and *Callosobruchuys chienensis*; Tenebrionidae such as *Tenebrio molitor* and *Tribolium castaneum*; Chrysomelidae such as *Oulema oryzae, Aulacophora femoralis, Phyllotreta striolata*, and *Leptinotarsa decemlineata*; Anobiidae; *Epilachna* spp. such as *Epilachna vigintioctopunctata*; Lyctidae; Bostrychidae; Cerambycidae; *Paederus fuscipes*;

Thysanoptera: Thripidae spp. including *Thrips* spp. such as *Thripspalmi, Frankliniella* spp. such as *Frankliniella occidentalis*, and *Sciltothrips* spp. such as *Sciltothrips dorsalis; Phlaeothripidae* spp.;

Hymenoptera: Tenthredinidae; Formicidae; Vespidae;

Dictyoptera: *Periplaneta* spp.; *Blatta* spp.;

Orthoptera: Acrididae; Gryllotalpidae;

Aphaniptera: *Pulex irritans*;
Anoplura: *Pediculus humanus*;
Isoptera: Termitidae;
Acarina: Tetranychidae.

The arthropod controlling composition of the present invention may be the present compound itself. The arthropod controlling composition of the present invention is usually produced by mixing the present compound, and a solid carrier, a liquid carrier, a gaseous carrier and/or bait (material for poison bait), if necessary, adding a surfactant and other adjuvant, and formulating to an oil solution, an emulsifiable concentrate, a flowable formulation, a wettable powder, a granule, a powder, a poison bait, a microcapsule and the like. In the pesticide composition of the present invention, the present compound is usually contained in an amount of 0.1% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, ammonium chloride, urea). The liquid carrier for formulation includes, for example, water, alcohols (e.g., methanol, ethanol, 2-propyl alcohol, ethylene glycol), ketones (e.g., acetone, methyl ethyl ketone, methyl isobutyl ketone, cyclohexanone), aromatic hydrocarbons (e.g., toluene, xylene, ethylbenzen, methylnaphthalene), aliphatic hydrocarbons (e.g., hexane, cyclohexane, kerosine, light oil), esters (e.g., ethyl acetate, butyl acetate), nitriles (e.g., acetonitrile, isobutyronitrile), ethers (e.g., ethylene glycol dimethyl ether, diisopropyl ether, 1,4-dioxane, tetrahydrofuran), acid amides (e.g., N,N-dimethylformamide, N,N-dimethylacetamide), halogenated hydrocarbons (e.g., dichloromethane, trichloroethane), dimethylsulfoxide, vegetable oils (e.g., soy bean oil, cotton seed oil).

The gaseous carrier for formulation includes, for example, fluorocarbons, butane gas, liquefied petroleum gas (LPG), dimethyl ether, carbon dioxide and the like.

The surfactant for formulation includes, for example, alkyl sulfate salts, alkylsulfonic acid salts, alkylarylsulfonic acid salts, alkyl aryl ethers and their polyoxyethylene derivatives, polyethylene glycol ethers, polyhydric alcohol esters, and sugar alcohol derivatives.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, sugars, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol), mineral oils, fatty acids, and fatty acid esters.

A base material for the poison bait includes, for example, grain powders, vegetable oils, sugars, and crystalline cellulose, and further, if necessary, antioxidants such as dibutylhydroxytoluene and nordihydroguaiaretic acid, preservatives such as dehydroacetic acid, agents for preventing children and pets from erroneously eating such as hot pepper powder, and pest-attractive flavors such as cheese flavor, onion flavor and peanut oil may be added to the base material.

The arthropod controlling composition is used by applying the arthropod controlling composition to pests directly and/or habitats of pests (e.g., nest, plant, soil). In the case of controlling the arthropod pest which is parasitic on a cultivating plant, for example, the arthropod controlling composition of the present invention is sprayed onto the upper side of the cultivating plant, pouring into the vicinities of a root of the cultivation plant.

When the pesticide composition of the present invention is used for a control of pests in agriculture and forestry, the application amount is usually 0.1 to 10,000 g as an active ingredient per 1,000 $m^2$. The emulsifiable concentrates, flowables, wettable powders and microcapsule formulations are usually applied after dilution with water to have an active ingredient concentration of 10 to 10,000 ppm, while oil solution, powders and granules are usually applied as such.

When the pesticide composition of the present invention is used for a control of epidemic, the application amount is usually 0.001 to 100 mg as an active ingredient per 1 $m^2$ in case of application for plane, and 0.001 to 10 mg as an active ingredient per 1 $m^3$ in case of application for open space surface. The emulsifiable concentrates, wettable powders and flowables are usually applied after dilution with water to have an active ingredient concentration of 0.01 to 100,000 ppm, while oil solutions, aerosols, smoking agents and poison baits are usually applied as such.

The pesticide composition of the present invention can also be used in admixture or combination with other insecticides, nematocides, acaricides, fungicides, herbicides, plant growth regulators, synergists, fertilizers, soil conditioners, animal feeds, and the like.

The active ingredients of such other insecticide and acaricide include, for example, organophosphorus compounds such as fenitrothion, fenthion, pyridaphenthion, diazinon, chlorpyrifos, chlorpyrifos-methyl, acephate, methidathion, disulfoton, DDVP, sulprofos, profenofos, cyanophos, dioxabenzofos, dimethoate, phenthoate, malathion, trichlorfon, azinphos-methyl, monocrotophos, dicrotophos, ethion, and fosthiazate; carbamate compounds such as BPMC, benfuracarb, propoxur, carbosulfan, carbaryl, methomyl, ethiofencarb, aldicarb, oxamyl, fenothiocarb, and thiodicarb; pyrethroid compounds such as etofenprox, fenvalerate, esfenvalerate, fenpropathrin, cypermethrin, alfa-cypermethrin, zeta-cypermethrin, permethrin, cyhalothrin, lambda-cyhalothrin, cyfluthrin, beta-cyfluthrin, deltamethrin, cycloprothrin, tau-fluvalinate, flucythrinate, bifenthrin, acrinathrin, tralomethrin, silafluofen, and halfenprox;

neonicotinoid compounds such as acetamiprid, thiamethoxam, and thiacloprid; benzoylphenylurea compounds such as chlorfluazuron, teflubenzuron, flufenoxuron, and lufenuron; benzoylhydrazide compounds such as tebufenozide, chromafenozide, methoxyfenozide and halofenozide; thiadiazine derivatives such as buprofezin; nereistoxin derivatives such as cartap, thiocyclam, and bensultap; chlorinated hydrocarbon compounds such as endosulfan, gamma-BHC, and 1,1-bis(chlorophenyl)-2,2,2-trichloroethanol; formamidine derivatives such as amitraz and chlordimeform; thiourea derivatives such as diafenthiuron; phenylpyrazole derivatives such as ethiprole, and acetoprole; chlorfenapyr; pymetrozine; spinosad; indoxacarb; bromopropylate; tetradifon; chinomethionat; propargite; fenbutatin oxide; hexythiazox; etoxazole; clofentezine; pyridaben; pyridalyl; fenpyroximate; tebufenpyrad; pyrimidifen; fenazaquin; acequinocyl; bifenazate; spirodiclofen; spiromesifen; milbemectin; avermectin; emamectin benzoate; azadirachtin; polynactin complexes such as tetranactin, dinactin, and trinactin; and the like.

The present invention will be further illustrated by the following production examples, formulation examples, and test examples; however, the present invention is not limited to these examples. In the following production examples, the data of ¹H-NMR were measured in a solvent of deuterium chloroform with tetramethylsilane as the internal standard.

Production Examples of the present compounds are exemplified.

PRODUCTION EXAMPLE 1

Into 11 ml of N,N-dimethylformamide were dissolved 190 mg of 5-chloro-3-methylthio-1,2,4-thiadiazole and 123 mg of benzyl alcohol, 59 mg of sodium hydride (60% in oil) was added thereto under ice-cooling, and the reaction mixture was stirred for 0.5 hour under ice-cooling and for 4.5 hours at room temperature. The reaction mixture was added to saturated ammonium chloride aqueous solution, and extracted with t-butyl methyl ether. The organic layer was concentrated, and the residue obtained was subjected to silica gel column chromatography to give 190 mg of 5-benzyloxy-3-methylthio-1,2,4-thiadiazole (hereinafter, referred to as the present compound (1)).

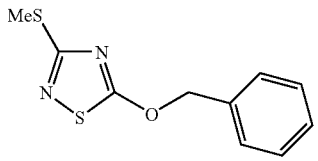

¹H-NMR: 7.43-7.38 (m, 5H), 5.49 (s, 2H), 2.62 (s, 3H)

PRODUCTION EXAMPLE 2

Into 2 ml of N,N-dimethylformamide was dissolved 215 mg of 2-chlorobenzyl alcohol, 59 mg of sodium hydride (60% in oil) was added thereto under ice-cooling. After stirring for 30 minutes, a solution of 250 mg of 5-chloro-3-methylthio-1,2,4-thiadiazole in 2 ml of N,N-dimethylformamide was added dropwise into the mixture and the reaction mixture was stirred for 0.5 hour under ice-cooling and for 2 hours at room temperature. The reaction mixture was added to saturated sodium chloride aqueous solution, and extracted with t-butyl methyl ether. The organic layer was concentrated, and the residue obtained was subjected to silica gel column chromatography to give 188 mg of 5-(2-chlorobenzyloxy)-3-methylthio-1,2,4-thiadiazole (hereinafter, referred to as the present compound (2)).

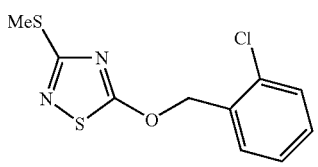

¹H-NMR: 7.53-7.29 (m, 4H), 5.61 (s, 2H), 2.62 (s, 3H)

PRODUCTION EXAMPLE 3

By using 215 mg of 3-chlorobenzyl alcohol instead of 2-chlorobenzyl alcohol according to Production Example 2 was obtained 190 mg of 5-(3-chlorobenzyloxy)-3-methylthio-1,2,4-thiadiazole (hereinafter, referred to as the present compound (3)).

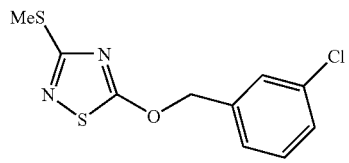

¹H-NMR: 7.45-7.30 (m, 4H), 5.47 (s, 2H), 2.61 (s, 3H)

PRODUCTION EXAMPLE 4

Into 2 ml of N,N-dimethylformamide were dissolved 150 mg of 5-chloro-3-methylthio-1,2,4-thiadiazole and 154 mg of 4-chlorobenzyl alcohol, 43 mg of sodium hydride (60% in oil) was added thereto under ice-cooling, and the reaction mixture was stirred for 0.5 hour under ice-cooling and for 4 hours at room temperature. The reaction mixture was added to saturated sodium chloride aqueous solution, and extracted with t-butyl methyl ether. The organic layer was concentrated, and the residue obtained was subjected to silica gel column chromatography to give 170 mg of 5-(4-chlorobenzyloxy)-3-methylthio-1,2,4-thiadiazole (hereinafter, referred to as the present compound (4)).

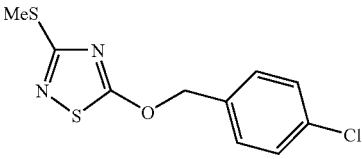

¹H-NMR: 7.37 (s, 4H), 5.46 (s, 2H), 2.61 (s, 3H)

PRODUCTION EXAMPLE 5

By using 264 mg of 2-trifluoromethybenzyl alcohol instead of 2-chlorobenzyl alcohol according to Production Example 2 was obtained 203 mg of 5-(2-trifluoromethylbenzyloxy)-3-methylthio-1,2,4-thiadiazole (hereinafter, referred to as the present compound (5)).

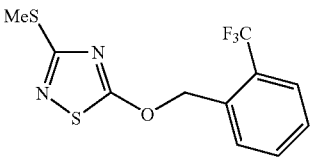

¹H-NMR: 7.76-7.49 (m, 4H), 5.68 (s, 2H), 2.61 (s, 3H)

PRODUCTION EXAMPLE 6

By using 264 mg of 3-trifluoromethybenzyl alcohol instead of 2-chlorobenzyl alcohol according to Production Example 2 was obtained 93 mg of 5-(3-trifluoromethylbenzyloxy)-3-methylthio-1,2,4-thiadiazole (hereinafter, referred to as the present compound (6)).

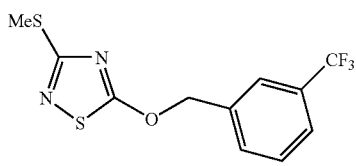

$^{1}$H-NMR: 7.73-7.50 (m, 4H), 5.55 (s, 2H), 2.61 (s, 3H)

PRODUCTION EXAMPLE 7

By using 264 mg of 4-trifluoromethybenzyl alcohol instead of 2-chlorobenzyl alcohol according to Production Example 2 was obtained 61 mg of 5-(4-trifluoromethylbenzyloxy)-3-methylthio-1,2,4-thiadiazole (hereinafter, referred to as the present compound (7)).

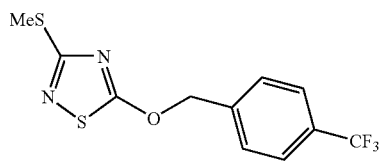

$^{1}$H-NMR: 7.67 (d, 2H), 7.56 (d, 2H), 5.56 (s, 2H), 2.61 (s, 3H)

PRODUCTION EXAMPLE 8

By using 131 mg of 4-methylbenzyl alcohol instead of 4-chlorobenzyl alcohol according to Production Example 4 was obtained 85 mg of 5-(4-methylbenzyloxy)-3-methylthio-1,2,4-thiadiazole (hereinafter, referred to as the present compound (8)).

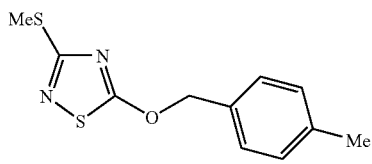

$^{1}$H-NMR: 7.33 (d, 2H), 7.21 (d, 2H), 5.44 (s, 2H), 2.61 (s, 3H)

PRODUCTION EXAMPLE 9

By using 246 mg of 4-tert-butylbenzyl alcohol instead of 2-chlorobenzyl alcohol according to Production Example 2 was obtained 264 mg of 5-(4-tert-butylbenzyloxy)-3-methylthio-1,2,4-thiadiazole (hereinafter, referred to as the present compound (9)).

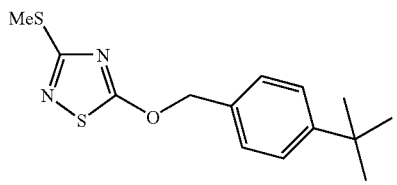

$^{1}$H-NMR: 7.44 (d, 2H), 7.38 (d, 2H), 5.46 (s, 2H), 2.68 (s, 3H) 1.34 (s, 9H)

PRODUCTION EXAMPLE 10

By using 207 mg of 4-methoxybenzyl alcohol instead of 2-chlorobenzyl alcohol according to Production Example 2 was obtained 179 mg of 5-(4-methoxybenzyloxy)-3-methylthio-1,2,4-thiadiazole (hereinafter, referred to as the present compound (10)).

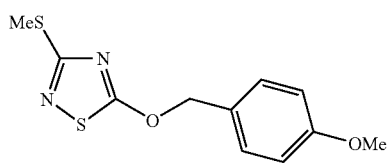

$^{1}$H-NMR: 7.49 (d, 2H), 7.92 (d, 2H), 5.44 (s, 2H), 3.82 (s, 3H) 2.61 (s, 3H)

PRODUCTION EXAMPLE 11

By using 231 mg of 4-methyothiobenzyl alcohol instead of 2-chlorobenzyl alcohol according to Production Example 2 was obtained 239 mg of 5-(4-methythiobenzyloxy)-3-methylthio-1,2,4-thiadiazole (hereinafter, referred to as the present compound (11)).

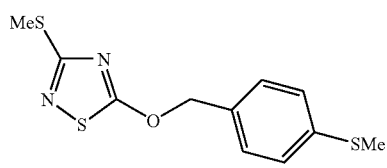

$^{1}$H-NMR: 7.36 (d, 2H), 7.24 (d, 2H), 5.42 (s, 2H), 2.62 (s, 3H) 2.49 (s, 3H)

PRODUCTION EXAMPLE 12

Into 3 ml of N,N-dimethylformamide were dissolved 334 mg of 5-chloro-3-methylthio-1,2,4-thiadiazole and 4-fluorobenzyl alcohol, 84 mg of sodium hydride (60% in oil) was added thereto under ice-cooling, and the reaction mixture was stirred for 1 hour under ice-cooling and for 4 hours at room temperature. The reaction mixture was added to saturated sodium chloride aqueous solution, and extracted with t-butyl methyl ether. The organic layer was concentrated, and the residue obtained was subjected to silica gel column chromatography to give 357 mg of 5-(4-fluorobenzyloxy)-

3-methylthio-1,2,4-thiadiazole (hereinafter, referred to as the present compound (12)).

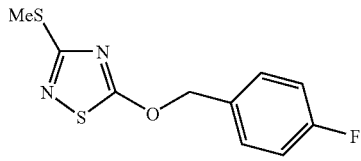

¹H-NMR: 7.43 (m, 2H), 7.09 (m, 2H), 5.46 (s, 2H), 2.61 (s, 3H)

PRODUCTION EXAMPLE 13

By using 374 mg of 4-bromobenzyl alcohol instead of 4-fluorobenzyl alcohol according to Production Example 12 was obtained 500 mg of 5-(4-bromobenzyloxy)-3-methylthio-1,2,4-thiadiazole (hereinafter, referred to as the present compound (13)).

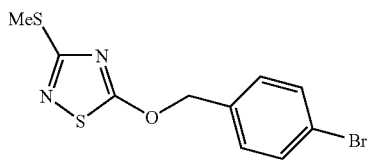

¹H-NMR: 7.53 (d, 2H), 7.32 (d, 2H), 5.44 (s, 2H), 2.61 (s, 3H)

PRODUCTION EXAMPLE 14

By using 468 mg of 4-iodobenzyl alcohol instead of 4-fluorobenzyl alcohol according to Production Example 12 was obtained 440 mg of 5-(4-iodobenzyloxy)-3-methylthio-1,2,4-thiadiazole (hereinafter, referred to as the present compound (14)).

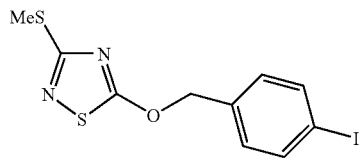

¹H-NMR: 7.74 (d, 2H), 7.19 (d, 2H), 5.43 (s, 2H), 2.61 (s, 3H)

PRODUCTION EXAMPLE 15

By using 384 mg of 4-trifluoromethoxybenzyl alcohol instead of 4-fluorobenzyl alcohol according to Production Example 12 was obtained 480 mg of 5-(4-trifluoromethoxybenzyloxy)-3-methylthio-1,2,4-thiadiazole. 5-(4-trifluoromethoxybenzyloxy)-3-methylthio-1,2,4-thiadiazole (hereinafter, referred to as the present compound (15)).

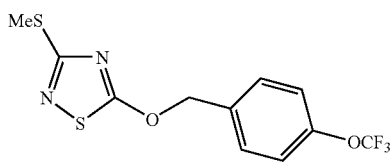

¹H-NMR: 7.48 (d, 2H), 7.23 (d, 2H), 5.49 (d, 2H), 2.61 (s, 3H)

PRODUCTION EXAMPLE 16

By using 216 mg of 2,6-difluorobenzyl alcohol instead of 4-chlorobenzyl alcohol according to Production Example 2 was obtained 254 mg of 5-(2,6-difluorobenzyloxy)-3-methylthio-1,2,4-thiadiazole (hereinafter, referred to as the present compound (16)).

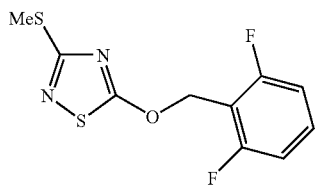

¹H-NMR: 7.44-7.32 (m, 1H), 6.99-6.92 (m, 2H), 5.60 (s, 2H), 2.63 (s, 3H)

PRODUCTION EXAMPLE 17

By using 216 mg of 3,5-difluorobenzyl alcohol instead of 4-chlorobenzyl alcohol according to Production Example 2 was obtained 108 mg of 5-(3,5-difluorobenzyloxy)-3-methylthio-1,2,4-thiadiazole (hereinafter, referred to as the present compound (17)).

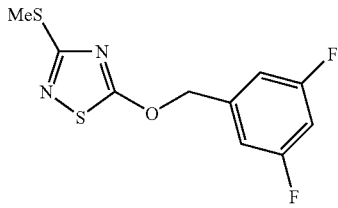

¹H-NMR: 6.96 (m, 2H), 6.81 (m, 1H), 5.47 (s, 2H), 2.61 (s, 3H)

PRODUCTION EXAMPLE 18

By using 266 mg of 3,4-dichlorobenzyl alcohol instead of 4-chlorobenzyl alcohol according to Production Example 2 was obtained 241 mg of 5-(3,4-dichlorobenzyloxy)-3-methylthio-1,2,4-thiadiazole (hereinafter, referred to as the present compound (18)).

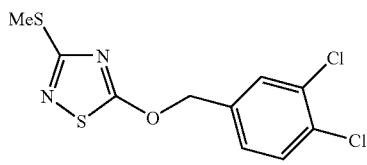

¹H-NMR: 7.55 (s, 1H), 7.48 (d, 1H), 7.28 (d, 1H), 5.44 (s, 2H), 2.61 (s, 3H)

PRODUCTION EXAMPLE 19

Into 2 ml of N,N-dimethylformamide was dissolved 218 mg of 2-pyridylmethanol, 84 mg of sodium hydride (60% in oil) was added thereto under ice-cooling. After stirring for 15 minutes, a solution of 334 mg of 5-chloro-3-methylthio- 1,2,4-thiadiazole in 2 ml of N,N-dimethylformamide was added dropwise into the mixture and the reaction mixture was stirred for 0.5 hour under ice-cooling and for 2 hours at room temperature. The reaction mixture was added to saturated sodium chloride aqueous solution, and extracted with t-butyl methyl ether. The organic layer was concentrated, and the residue obtained was subjected to silica gel column chromatography to give 30 mg of 5-(2-pyridylmethyloxy)-3-methylthio-1,2,4-thiadiazole (hereinafter, referred to as the present compound (19)).

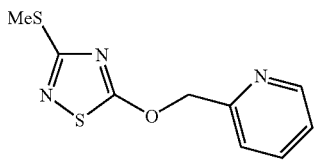

$^1$H-NMR: 8.64 (d, 1H), 7.77 (t, 1H), 7.46 (d, 1H), 7.28 (t, 1H), 5.60 (s, 2H), 2.61 (s, 3H)

PRODUCTION EXAMPLE 20

Into 2 ml of N,N-dimethylformamide were dissolved 100 mg of 5-chloro-3-methylthio-1,2,4-thiadiazole and 78 mg of 3-pyridinemethanol, 78 mg of sodium hydride (60% in oil) was added thereto under ice-cooling, and the reaction mixture was stirred for 0.5 hour under ice-cooling and for 1 hours at room temperature. The reaction mixture was added to saturated ammonium chloride aqueous solution, and extracted with t-butyl methyl ether. The organic layer was concentrated, and the residue obtained was subjected to silica gel column chromatography to give 88 mg of 5-(3-pyridylmethyl)-3-methylthio-1,2,4-thiadiazole (hereinafter, referred to as the present compound (20)).

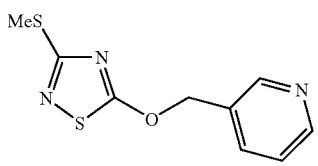

$^1$H-NMR: 8.72 (s, 1H), 8.64 (d, 1H), 7.81 (d, 1H), 7.35 (t, 1H), 5.53 (s, 2H), 2.61 (s, 3H)

PRODUCTION EXAMPLE 21

Into 2.5 ml of N,N-dimethylformamide were dissolved 200 mg of 5-chloro-3-methylthio-1,2,4-thiadiazole and 207 mg of 4-chloro-3-pyridylmethyl alcohol, 59 mg of sodium hydride (60% in oil) was added thereto under ice-cooling, and the reaction mixture was stirred for 0.5 hour under ice-cooling and for 1 hour at room temperature. The reaction mixture was added to saturated ammonium chloride aqueous solution, and extracted with t-butyl methyl ether. The organic layer was concentrated, and the residue obtained was subjected to silica gel column chromatography to give 170 mg of 5-(6-chloro-3-pyridyl)methyloxy-3-methylthio-1,2,4-thiadiazole (hereinafter, referred to as the present compound (21)).

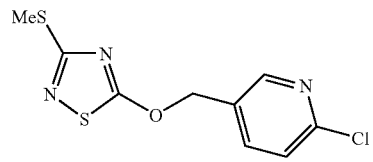

$^1$H-NMR: 8.50 (d, 1H), 7.77 (dd, 1H), 7.38 (d, 1H), 5.50 (s, 2H), 2.61 (s, 3H)

PRODUCTION EXAMPLE 22

By using 176 mg of 1-phenylethanol instead of 6-chloro-3-pyridylmethyl alcohol according to Production Example 21 was obtained 190 mg of 5-(1-phenylethoxy)-3-methylthio-1,2,4-thiadiazole (hereinafter, referred to as the present compound (22)).

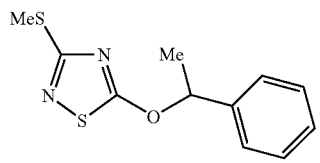

$^1$H-NMR: 7.44-7.29 (m, 5H), 5.99 (q, 1H), 2.58 (s, 3H), 1.74 (d, 3H)

PRODUCTION EXAMPLE 23

By using 131 mg of 2-phenylethanol instead of benzyl alcohol according to Production Example 4 was obtained 160 mg of 5-(2-phenylethoxy)-3-methylthio-1,2,4-thiadiazole (hereinafter, referred to as the present compound (23)).

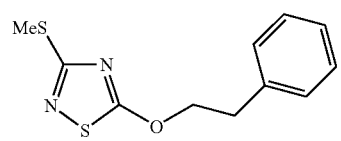

$^1$H-NMR: 7.36-7.23 (m, 5H), 4.67 (t, 2H), 3.13 (t, 2H), 2.60 (s, 3H)

PRODUCTION EXAMPLE 24

By using 246 mg of 2-pyridyl-2-ethanol instead of 2-pyridylmethanol according to Production Example 19 was obtained 45 mg of 5-(2-pyridyl-2-ethyloxy)-3-methylthio-1,2,4-thiadiazole (hereinafter, referred to as the present compound (24)).

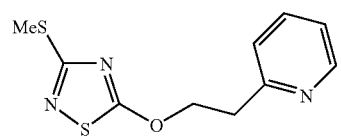

$^1$H-NMR: 8.56 (d, 1H), 7.63 (t, 1H), 7.17 (m, 2H), 4.88 (t, 2H), 3.31 (t, 2H), 2.60 (s, 3H)

PRODUCTION EXAMPLE 25

By using 196 mg of 3-phenylpropanol instead of 6-chloro-3-pyridylmethyl alcohol according to Production Example 21 was obtained 210 mg of 5-(3-phenylpropyloxy)-3-methylthio-1,2,4-thiadiazole (hereinafter, referred to as the present compound (25)).

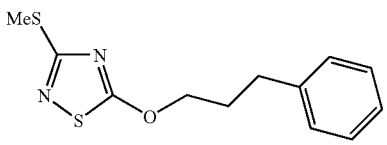

¹H-NMR: 7.30-7.18 (m, 5H), 4.47 (t, 2H), 2.77 (t, 2H), 2.60 (s, 3H), 2.15 (m, 2H)

PRODUCTION EXAMPLE 26

Into 4 ml of N,N-dimethylformamide were dissolved 334 mg of 5-chloro-3-methylthio-1,2,4-thiadiazole and 3-nitrobenzyl alcohol, 331 mg of potassium carbonate was added thereto under, and the reaction mixture was stirred for 4 hours at room temperature. The reaction mixture was added to saturated sodium chloride aqueous solution, and extracted with t-butyl methyl ether. The organic layer was concentrated, and the residue obtained was subjected to silica gel column chromatography to give 320 mg of 5-(3-nitrobenzyloxy)-3-methylthio-1,2,4-thiadiazole (hereinafter, referred to as the present compound (26)).

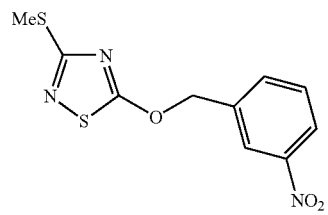

¹H-NMR: 8.33 (s, 1H), 8.24 (d, 1H), 7.79 (d, 1H), 7.60 (t, 1H), 5.60 (s, 2H), 2.62 (s, 3H)

PRODUCTION EXAMPLE 27

By using 337 mg of 4-nitrobenzyl alcohol instead of 3-nitrobenzyl alcohol according to Production Example 26 was obtained 36 mg of 5-(4-nitrobenzyloxy)-3-methylthio-1,2,4-thiadiazole (hereinafter, referred to as the present compound (27)).

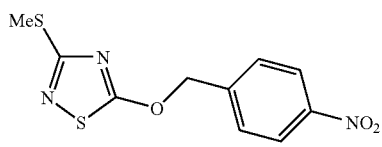

¹H-NMR: 8.27 (d, 2H), 7.62 (d, 2H), 5.61 (s, 2H), 2.61 (s, 3H)

PRODUCTION EXAMPLE 28

Into 4 ml of N,N-dimethylformamide were dissolved 334 mg of 5-chloro-3-methylthio-1,2,4-thiadiazole and 389 mg of 3,5-dichlorobenzyl alcohol, 96 mg of sodium hydride (60% in oil) was added thereto under ice-cooling, and the reaction mixture was stirred for 0.5 hour under ice-cooling and for 4 hours at room temperature. The reaction mixture was added to saturated sodium chloride aqueous solution, and extracted with t-butyl methyl ether. The organic layer was concentrated, and the residue obtained was subjected to silica gel column chromatography to give 380 mg of 5-(3,5-dichlorobenzyloxy)-3-methylthio-1,2,4-thiadiazole (hereinafter, referred to as the present compound (28)).

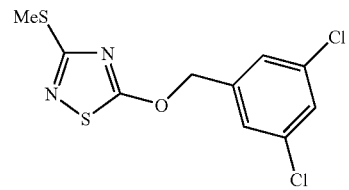

¹H-NMR: 7.37 (s, 1H), 7.33 (s, 2H), 5.44 (s, 2H), 2.61 (s, 3H)

PRODUCTION EXAMPLE 29

By using 389 mg of 2,4-dichlorobenzyl alcohol instead of 3,5-dichlorobenzyl alcohol according to Production Example 28 was obtained 370 mg of 5-(2,4-dichlorobenzyloxy)-3-methylthio-1,2,4-thiadiazole (hereinafter, referred to as the present compound (29)).

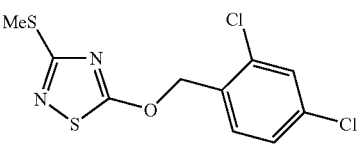

¹H-NMR: 7.46 (d, 2H), 7.29 (d, 1H), 5.56 (s, 2H), 2.61 (s, 3H)

PRODUCTION EXAMPLE 30

Into 4 ml of N,N-dimethylformamide were dissolved 193 mg of 5-chloro-3-allylthio-1,2,4-thiadiazole and 108 mg of benzyl alcohol, 48 mg of sodium hydride (60% in oil) was added thereto under ice-cooling, and the reaction mixture was stirred for 1 hour under ice-cooling. The reaction mixture was added to saturated sodium chloride aqueous solution, and extracted with t-butyl methyl ether. The organic layer was concentrated, and the residue obtained was subjected to silica gel column chromatography to give 240 mg of 5-benzyloxy-3-allylthio-1,2,4-thiadiazole (hereinafter, referred to as the present compound (30)).

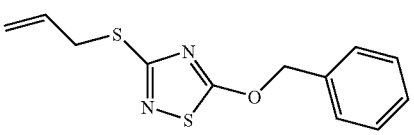

¹H-NMR: 7.51-7.28 (m, 5H), 5.99 (m, 1H), 5.49 (s, 2H), 5.33 (d, 1H), 5.16 (d, 1H), 3.84 (d, 2H)

PRODUCTION EXAMPLE 31

Into 3 ml of N,N-dimethylformamide were dissolved 243 mg of 5-chloro-3-benzylthio-1,2,4-thiadiazole and 108 mg of benzyl alcohol, 48 mg of sodium hydride (60% in oil) was added thereto under ice-cooling, and the reaction mixture was stirred for 1 hour under ice-cooling and for 17 hours at room temperature. The reaction mixture was added to saturated sodium chloride aqueous solution, and extracted with t-butyl methyl ether. The organic layer was concentrated, and the residue obtained was subjected to silica gel column chromatography to give 146 mg of 5-benzyloxy-3-benzylthio-1,2,4-thiadiazole (hereinafter, referred to as the present compound (31)).

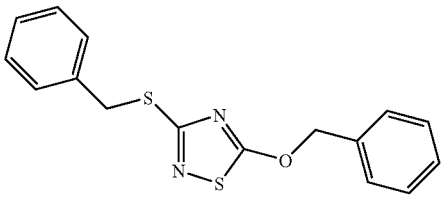

$^1$H-NMR: 7.42-7.25 (m, 10H), 5.48 (s, 2H), 4.42 (s, 2H)

PRODUCTION EXAMPLE 32

Into 3 ml of N,N-dimethylformamide were dissolved 416 mg of 5-chloro-3-(4-chlorobenzylthio)-1,2,4-thiadiazole and 162 mg of benzyl alcohol, 48 mg of sodium hydride (60% in oil) was added thereto under ice-cooling, and the reaction mixture was stirred for 15 minutes under ice-cooling and for 1 hour at room temperature. The reaction mixture was added to saturated sodium chloride aqueous solution, and extracted with t-butyl methyl ether. The organic layer was concentrated, and the residue obtained was subjected to silica gel column chromatography to give 400 mg of 5-benzyloxy-3-(4-chlorobenzyl)thio-1,2,4-thiadiazole (hereinafter, referred to as the present compound (32)).

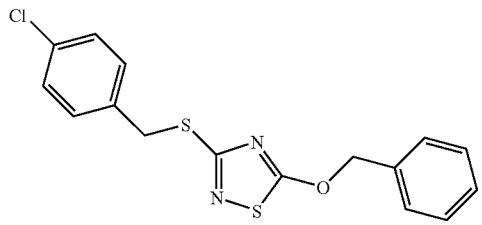

$^1$H-NMR: 7.43-7.26 (m, 9H), 5.48 (s, 2H), 4.37 (s, 2H)

PRODUCTION EXAMPLE 33

Into 2 ml of N,N-dimethylformamide were dissolved 200 mg of 5-chloro-3-(4-methoxybenzyl)thio-1,2,4-thiadiazole and 87 mg of benzyl alcohol, 35 mg of sodium hydride (60% in oil) was added thereto under ice-cooling, and the reaction mixture was stirred for 1 hour under ice-cooling and for 4 hours at room temperature. The reaction mixture was added to saturated sodium chloride aqueous solution, and extracted with t-butyl methyl ether. The organic layer was concentrated, and the residue obtained was subjected to silica gel column chromatography to give 165 mg of 5-benzyloxy-3-(4-methoxybenzyl)thio-1,2,4-thiadiazole (hereinafter, referred to as the present compound (33)).

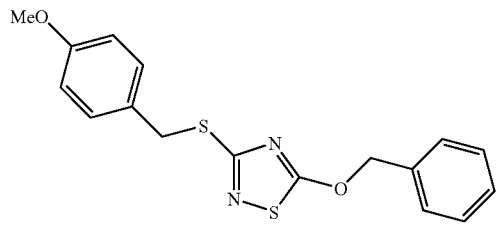

$^1$H-NMR: 7.51-7.31 (m, 7H), 6.83 (d, 2H), 5.48 (s, 2H), 4.38 (s, 2H), 3.79 (s, 3H)

PRODUCTION EXAMPLE 34

Into 4 g of N,N-dimethylformamide was dissolved 218 mg of 4-pyridinemethanol, 96 mg of sodium hydride (60% in oil) was added thereto at room temperature. After stirring for 30 minutes, a solution of 334 mg of 5-chloro-3-methylthio-1,2,4-thiadiazole in 1 g of N,N-dimethylformamide was added dropwise into the mixture and the reaction mixture was stirred for 4 hours at room temperature. The reaction mixture was added to saturated sodium chloride aqueous solution, and extracted with t-butyl methyl ether. The organic layer was concentrated, and the residue obtained was subjected to silica gel column chromatography to give 260 mg of 5-(4-pyridylmethyloxy)-3-methylthio-1,2,4-thiadiazole (hereinafter, referred to as the present compound (34)).

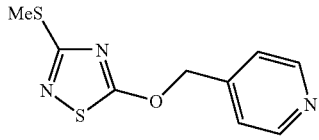

$^1$H-NMR: 8.65 (d, 2H), 7.33 (d, 2H), 5.53 (s, 2H), 2.61 (s, 3H)

PRODUCTION EXAMPLE 35

Into 3 g of N,N-dimethylformamide were dissolved 251 mg of 5-chloro-3-methylthio-1,2,4-thiadiazole and 188 mg of 6-chloro-2-pyridylmethyl alcohol, 72 mg of sodium hydride (60% in oil) was added thereto at room temperature, and the reaction mixture was stirred for 30 minutes. The reaction mixture was added to saturated sodium chloride aqueous solution, and extracted with t-butyl methyl ether. The organic layer was concentrated, and the residue obtained was subjected to silica gel column chromatography to give 44 mg of 5-(6-chloro-2-pyridylmethyloxy)-3-methylthio-1,2,4-thiadiazole (hereinafter, referred to as the present compound (35)).

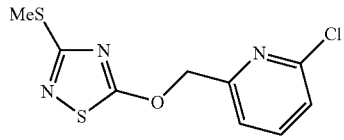

$^1$H-NMR: 7.71 (t, 1H), 7.38 (d, 1H), 7.30 (d, 1H), 5.55 (s, 2H), 2.60 (s, 3H)

PRODUCTION EXAMPLE 36

Into 3.6 g of N,N-dimethylformamide were dissolved 304 mg of 5-chloro-3-methylthio-1,2,4-thiadiazole and 200 mg of 2-pyrimidylmethyl alcohol, 87 mg of sodium hydride (60% in oil) was added thereto under ice-cooling, and the reaction mixture was stirred for 15 minutes. After stirring for 1.5 hour at room temperature, the reaction mixture was added to saturated sodium chloride aqueous solution, and extracted with t-butyl methyl ether. The organic layer was concentrated, and the residue obtained was subjected to silica gel column chromatography to give 278 mg of 5-(2-pyrimidylmethyloxy)-3-methylthio-1,2,4-thiadiazole (hereinafter, referred to as the present compound (36)).

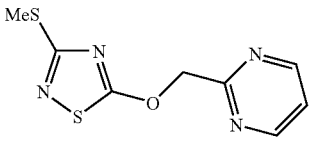

$^1$H-NMR: 8.78 (d, 2H), 7.27 (t, 1H), 5.73 (s, 2H), 2.59 (s, 3H)

PRODUCTION EXAMPLE 37

Into 4 g of N,N-dimethylformamide were dissolved 304 mg of 5-chloro-3-methylthio-1,2,4-thiadiazole and 200 mg of 5-pyrimidylmethyl alcohol, 97 mg of sodium hydride (60% in oil) was added thereto under ice-cooling, and the reaction mixture was stirred for 30 minutes. After stirring for 5 hours at room temperature, the reaction mixture was added to saturated sodium chloride aqueous solution, and extracted with t-butyl methyl ether. The organic layer was concentrated, and the residue obtained was subjected to silica gel column chromatography to give 210 mg of 5-(5-pyrimidylmethyloxy)-3-methylthio-1,2,4-thiadiazole (hereinafter, referred to as the present compound (37)).

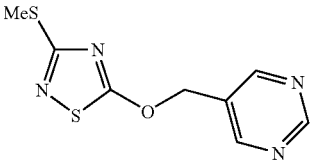

$^1$H-NMR: 9.25 (s, 1H), 8.88 (s, 2H), 7.27 (s, 2H), 2.61 (s, 3H)

PRODUCTION EXAMPLE 38

Into 2 g of N,N-dimethylformamide were dissolved 219 mg of 5-chloro-3-benzylthio-1,2,4-thiadiazole and 200 mg of 5-pyrimidylmethyl alcohol, 44 mg of sodium hydride (60% in oil) was added thereto under ice-cooling, and the reaction mixture was stirred for 30 minutes. After stirring for 5 hours at room temperature, the reaction mixture was added to saturated sodium chloride aqueous solution, and extracted with t-butyl methyl ether. The organic layer was concentrated, and the residue obtained was subjected to silica gel column chromatography to give 130 mg of 5-(5-pyrimidylmethyloxy)-3-benzylthio-1,2,4-thiadiazole (hereinafter, referred to as the present compound (38)).

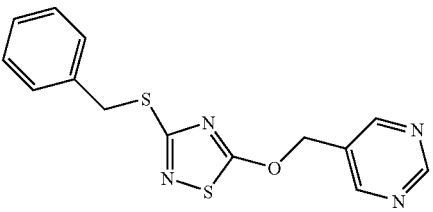

H-NMR: 9.25 (s, 1H), 8.86 (s, 2H), 7.43-7.24 (m, 5H), 5.53 (s, 2H), 4.41 (s, 2H)

PRODUCTION EXAMPLE 39

Into 4 g of N,N-dimethylformamide were dissolved 304 mg of 5-chloro-3-methylthio-1,2,4-thiadiazole and 200 mg of 4-pyrimidylmethyl alcohol, 87 mg of sodium hydride (60% in oil) was added thereto under ice-cooling, and the reaction mixture was stirred for 15 minutes. After stirring for 2 hours at room temperature, the reaction mixture was added to saturated sodium chloride aqueous solution, and extracted with t-butyl methyl ether. The organic layer was concentrated, and the residue obtained was subjected to silica gel column chromatography to give 210 mg of 5-(4-pyrimidylmethyloxy)-3-methylthio-1,2,4-thiadiazole (hereinafter, referred to as the present compound (39)).

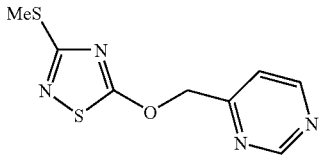

$^1$H-NMR: 9.21 (s, 1H), 8.78 (d, 1H), 7.45 (d, 1H), 5.60 (s, 2H), 2.60 (s, 3H)

PRODUCTION EXAMPLE 40

By using 219 mg of 5-chloro-3-benzylthio-1,2,4-thiadiazole instead of 5-chloro-3-methylthio-1,2,4-thiadiazole according to Production Example 39 was obtained 110 mg of 5-(4-pyrimidylmethyloxy)-3-benzylthio-1,2,4-thiadiazole (hereinafter, referred to as the present compound (40)).

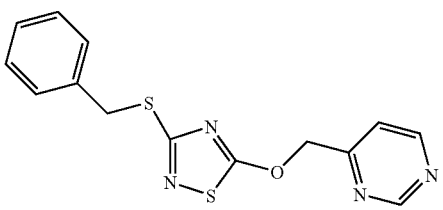

$^1$H-NMR: 9.21 (s, 1H), 8.77 (d, 1H), 7.44-7.23 (m, 6H), 5.59 (s, 2H), 4.39 (s, 2H)

PRODUCTION EXAMPLE 41

By using 252 mg of 5-chloro-3-(4-chlorobenzylthio)-1,2,4-thiadiazole instead of 5-chloro-3-methylthio-1,2,4-thiadiazole according to Production Example 40 was obtained 127 mg of 5-(4-pyrimidylmethyloxy)-3-(4-chlorobenzyl)thio-1,2,4-thiadiazole (hereinafter, referred to as the present compound (41)).

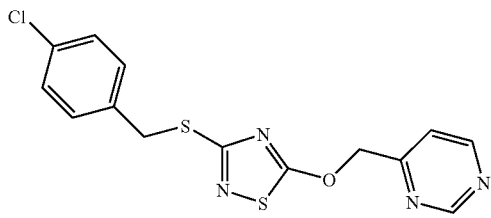

¹H-NMR: 9.21 (s, 1H), 8.78 (d, 1H), 7.43-7.24 (m, 5H), 5.58 (s, 2H), 4.34 (s, 2H)

PRODUCTION EXAMPLE 42

Into 3 g of N,N-dimethylformamide were dissolved 300 mg of 5-chloro-3-ethoxymethylthio-1,2,4-thiadiazole and 153 mg of benzyl alcohol, 68 mg of sodium hydride (60% in oil) was added thereto under ice-cooling, and the reaction mixture was stirred for 15 minutes. After stirring for 2 hours at room temperature, the reaction mixture was added to saturated sodium chloride aqueous solution, and extracted with t-butyl methyl ether. The organic layer was concentrated, and the residue obtained was subjected to silica gel column chromatography to give 210 mg of 5-benzylloxy-3-ethoxymethylthio-1,2,4-thiadiazole (hereinafter, referred to as the present compound (42)).

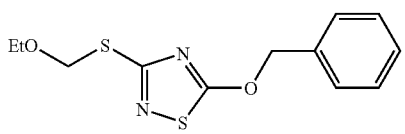

¹H-NMR: 7.46-7.36 (m, 5H), 5.49 (s, 2H), 5.40 (s, 2H), 3.67 (q, 2H), 1.24 (t, 3H)

PRODUCTION EXAMPLE 43

Into 3 g of N,N-dimethylformamide were dissolved 350 mg of 5-chloro-3-benzyloxymethylthio-1,2,4-thiadiazole and 153 mg of benzyl alcohol, 68 mg of sodium hydride (60% in oil) was added thereto under ice-cooling, and the reaction mixture was stirred for 30 minutes. After stirring for 2 hours at room temperature, the reaction mixture was added to saturated sodium chloride aqueous solution, and extracted with t-butyl methyl ether. The organic layer was concentrated, and the residue obtained was subjected to silica gel column chromatography to give 260 mg of 5-bezyloxy-3-benzyloxymethythio-1,2,4-thiadiazole (hereinafter, referred to as the present compound (43)).

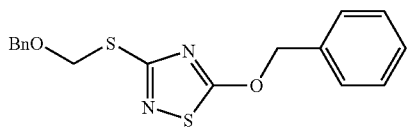

¹H-NMR: 7.45-7.25 (m, 10H), 5.49 (s, 2H), 5.43 (s, 2H), 4.71 (s, 2H)

PRODUCTION EXAMPLE 44

Into 1.5 g of acetic anhydride were added 620 mg of 2,6-lutidine and 500 mg of 5-benzyloxy-3-methylsulfinyl-1,2,4-thiadiazole under ice-cooling. After stirring for 15 hours at room temperature, the reaction mixture was added to saturated sodium hydrogen carbonate aqueous solution, and extracted with t-butyl methyl ether. The organic layer was concentrated, and the residue obtained was subjected to silica gel column chromatography to give 376 mg of 5-bezyloxy-3-acetoxymethythio-1,2,4-thiadiazole (hereinafter, referred to as the present compound (44)).

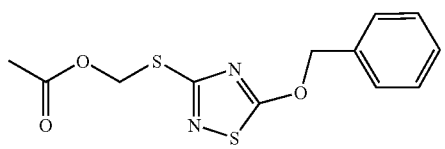

¹H-NMR: 7.46-7.36 (m, 5H), 5.77 (s, 2H), 5.50 (s, 2H), 2.11 (s, 3H)

Next, the production of the intermediate of the present compound is described as Reference Production Examples.

REFERENCE PRODUCTION EXAMPLE 1

Into the mixture of 20 ml of toluene and 10 ml of water were added 2.53 g of 4-methoxybenzylisothiourea hydrogen chloride, 2.03 g of perchloromethyl mercaptan, and 50 mg of benzyltriethylammonium chloride, and a solution of 1.74 g of sodium hydroxide in 10 ml of water was added dropwise to the mixture at about 0° C. over 4 hours. After the addition, the mixture was stirred for 1 hour at room temperature. Into the reaction mixture was added t-butyl methyl ether, and extracted. The organic layer was dried over anhydrous sodium sulfate, concentrated, and the residue obtained was subjected to silica gel column chromatography to give 5.38 g of 5-chloro-3-(4-methoxybenzyl)thio-1,2,4-thiadiazole.

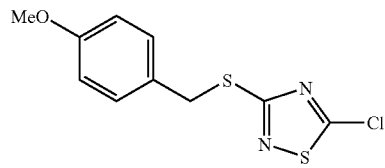

¹H-NMR: 7.35 (d, 2H), 6.85 (d, 2H), 4.41 (s, 2H), 3.79 (s, 3H)

REFERENCE PRODUCTION EXAMPLE 2

Into the mixture of 35 ml of water and 70 ml of dichloromethane were added 12.2 g of ethoxymethylisothiourea hydrogen chloride and 13.2 g of perchloromethyl mercaptan, and a solution of 11.4 g of sodium hydroxide in 35 ml of water was added dropwise to the mixture at about 0° C. over 1.5 hour. After the addition, the mixture was stirred for 1 hour at room temperature. Into the reaction mixture was added chloroform, and extracted. The organic layer was dried over anhydrous sodium sulfate, concentrated, and the residue obtained was subjected to silica gel column chromatography to give 5.22 g of 5-chloro-3-ethoxymethylthio-1,2,4-thiadiazole. 5-chloro-3-ethoxymethylthio-1,2,4-thiadiazole

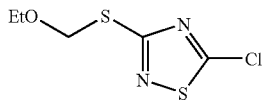

$^1$H-NMR: 5.43 (s, 2H), 3.68 (q, 2H), 1.26 (t, 3H)

REFERENCE PRODUCTION EXAMPLE 3

Into the mixture of 25 ml of water and 50 ml of dichloromethane were added 11.3 g of benzyloxymethylisothiourea hydrogen chloride and 9.02 g of perchloromethyl mercaptan, and a solution of 7.76 g of sodium hydroxide in 25 ml of water was added dropwise to the mixture at about 0° C. over 1.5 hour. After the addition, the mixture was stirred for 1 hour at room temperature. Into the reaction mixture was added chloroform, and extracted. The organic layer was dried over anhydrous sodium sulfate, concentrated, and the residue obtained was subjected to silica gel column chromatography to give 3.51 g of 5-chloro-3-benzyloxymethylthio-1,2,4-thiadiazole.

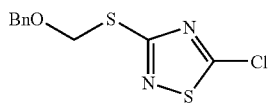

$^1$H-NMR: 7.36-7.28 (m, 5H), 5.45 (s, 2H), 4.69 (s, 2H)

REFERENCE PRODUCTION EXAMPLE 4

Into 12 ml of chloroform was dissolved 1.39 g of 5-benzyloxy-3-methylthio-1,2,4-thiadiazole, and metachloroperbenzoic acid (>70%) was slowly added to the mixture under ice-cooling. After stirring for 1 hour, the compound of low-polarity from the reaction mixture was detected by thin layer chromatography. The reaction mixture was poured into a saturated sodium sulfite aqueous solution, and separated. The organic layer was washed with sodium hydrogen carbonate aqueous solution, dried over anhydrous sodium sulfate, concentrated to give 1.4 g of 5-benzyloxy-3-methylsulfinyl-1,2,4-thiadiazole.

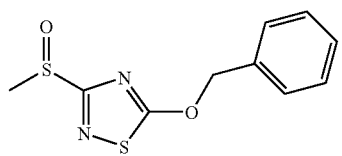

Next, Formulation Examples will be shown below. Parts are by weight.

FORMULATION EXAMPLE 1

Each 9 parts of the present compounds (1) to (44) were dissolved in 37.5 parts of xylene and 37.5 parts of dimethylformamide, and to this was added 10 parts of polyoxyethylene styrylphenyl ether and 6 parts of calcium dodecylbenzenesulfonate, and they were mixed thoroughly to obtain an emulsifiable concentrate.

FORMULATION EXAMPLE 2

Each 9 parts of the present compounds (1) to (44) were dissolved in a mixture of 4 parts of sodium laureate, 2 parts of calcium ligninsulfonate, 20 parts of a synthetic water-containing silicon oxide fine powder, and 65 parts of diatomaceous earth, and they were mixed thoroughly to obtain a wettable powder.

FORMULATION EXAMPLE 3

Each 3 parts of the present compounds (1) to (44) were dissolved in a mixture of 5 parts of a synthetic water-containing silicon oxide fine powder, 5 parts of sodium dodecylbenzeneuslfonate, 30 parts of bentonite, and 57 parts of clay, and they were mixed thoroughly, then, suitable amount of water was added to the mixture thereof, the resulted mixture was further stirred, granulated in a granulator, and dried under ventilation to obtain a granule.

FORMULATION EXAMPLE 4

Each 4.5 parts of the present compounds (1) to (44), 1 part of a synthetic water-containing silicon oxide fine powder, 1 part of DRILESS B (manufactured by Sankyo Co., Ltd.) and 7 parts of clay were mixed thoroughly in a mortar, then, stirred to mix by a juice mixer. To the resulted mixture was added 86.5 parts of cut clay, they were sufficiently stirred to mix, to obtain a powder.

FORMULATION EXAMPLE 5

Each 10 parts of the present compounds (1) to (44), 35 parts of white carbon containing 50 parts of ammonium polyoxyethylene alkyl ether sulfate, and 55 parts of water were mixed and finely ground according to a wet grinding method, to obtain a formulation.

FORMULATION EXAMPLE 6

Each 0.5 part of the present compounds (1) to (44) is dissolved in 10 parts of dichloromethane and mixed with 89.5 parts of Isoper M (isoparafin; trademark of Exxon chemicals), to obtain a oil solution.

FORMULATION EXAMPLE 7

An aerosol vessel is filled with each 0.5 part of the present compound (1) to (44) and 49.9 parts of Neothiozol (manufactured by Chuo Kasei Co.). The vessel is then equipped with a valve, 25 parts of dimethyl ether and 25 parts of liquefied petroleum gas are charged into the aerosol vessel, and the aerosol vessel is shaken and equipped with an actuator to give oil-based aerosol.

FORMULATION EXAMPLE 8

An aerosol vessel is filled with a solution of each 0.5 part of the present compound (1) to (44), 0.01 part of BHT, 5 parts of xylene, 3.39 parts of deodorized kerosene and 1 part of an emulsifiable agent (Atmos 300, trademark of Atlas Chemical Co.), and 50 parts of water. The vessel is then equipped with a valve and 40 parts of propellant (liquefied petroleum gas) is charged through the valve into the aerosol vessel under pressure to give water-based aerosol.

Next, the use example of the present compound as the arthropod pests controlling composition is showed by a Test Example.

TEST EXAMPLE

Each formulation of the present compound (1), (3), (4), (6), (7), (8), (12), (13), (14), (15), (16), (17), (18), (19), (20), (21), (22), (23), (24), (25), (26), (28), (30), (31), (33), (34), (35), (36), (37), (38), (42), (43) and (44) obtained according to the Formulation Example 5 was diluted with water so that the active ingredient concentration came to 500 ppm to prepare a diluting liquid.

The seeds of cucumber were planted in polyethylene cups and grown until their first foliage leaves developed, on which about 20 cotton aphids (*Aphis gossypii*) were made parasitic. After one day, the diluting liquid was sprayed at the rate of 20 ml/cup onto the cucumber plants. On the 6th day after the application, the number of cotton aphids was examined. As a result, the numbers of the living cotton aphids were three or less.

INDUSTRIAL APPLICABILITY

By using the present compounds, arthropod pests can be controlled.

The invention claimed is:

1. A thiadiazole compound of the formula (A):

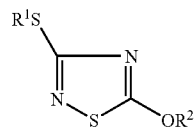

(A)

wherein $R^1$ represents methyl, $C_3$-$C_7$ alkenyl, $C_2$-$C_7$ alkoxyalkyl, $C_2$-$C_7$ alkylthioalkyl, $C_4$-$C_7$ alkoxyalkoxyalkyl, $C_4$-$C_7$ alkylthioalkoxyalkyl, phenyl $C_1$-$C_2$ alkyl, phenyloxy $C_1$-$C_2$ alkyl, phenyl $C_2$-$C_3$ alkoxyalkyl, wherein the phenyl group or the phenyloxy group is optionally substituted, or the substituent of the formula (B):

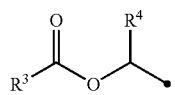

(B)

wherein $R^3$ represents $C_1$-$C_3$ alkyl, and $R^4$ represents a hydrogen atom, methyl, ethyl or optionally substituted phenyl; and $R^2$ represents phenyl $C_1$-$C_4$ alkyl, wherein the phenyl group is optionally substituted.

2. The thiadiazole compound according to claim 1, wherein the phenyl group in $R^2$ is optionally substituted with one or more selected from the group consisting of $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, nitro, cyano and halogen atoms.

3. The thiadiazole compound according to claim 1, wherein the phenyl group in $R^2$ is optionally substituted with one or more selected from the group consisting of $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy and halogen atoms.

4. The thiadiazole compound according to claim 1, wherein $R^1$ is methyl.

5. The thiadiazole compound according to claim 1, wherein $R^1$ is $C_3$-$C_7$ alkenyl, $C_2$-$C_7$ alkoxyalkyl, $C_2$-$C_7$ alkylthioalkyl, $C_4$-$C_7$ alkoxyalkoxyalkyl, or $C_4$-$C_7$ alkylthioalkoxyalkyl.

6. The thiadiazole compound according to claim 1, wherein $R^1$ is phenyl $C_1$-$C_2$ alkyl, phenyloxy $C_1$-$C_2$ alkyl, or phenyl $C_2$-$C_3$ alkoxyalkyl, wherein the phenyl group or the phenyloxy group is optionally substituted with one or more selected from the group consisting of $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, nitro, cyano and halogen atoms.

7. The thiadiazole compound according to claim 1, wherein $R^1$ is the substituent of the formula (B):

(B)

wherein $R^3$ represents $C_1$-$C_3$ alkyl, and $R^4$ represents a hydrogen atom, methyl, ethyl, or phenyl optionally substituted with one or more selected from the group consisting of $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, nitro, cyano and halogen atoms.

8. The thiadiazole compound according to claim 1, wherein $R^1$ is ($C_1$-$C_6$ alkoxy)methyl or ($C_1$-$C_6$ alkylthio) methyl.

9. The thiadiazole compound according to claim 1, wherein $R^1$ is benzyl, phenyloxymethyl, or benzyloxymethyl, optionally substituted with one or more selected from the group consisting of $C_1$-$C_4$ alkyl, $C_1$-$C_4$ haloalkyl, $C_1$-$C_4$ alkoxy, $C_1$-$C_4$ alkylthio, $C_1$-$C_4$ haloalkoxy, nitro, cyano and halogen atoms.

10. An arthropod controlling composition containing an effective amount of the thiadiazole compound according to claim 1.

11. A method for controlling an arthropod pest comprising applying an effective amount of the thiadiazole compound according to claim 1 to the arthropod pest or the habitats of the arthropod pest.

* * * * *